US010058457B2

(12) United States Patent
Schuren et al.

(10) Patent No.: US 10,058,457 B2
(45) Date of Patent: Aug. 28, 2018

(54) COMPRESSION DEVICE

(71) Applicant: 3M INNOVATIVE PROPERTIES COMPANY, Saint Paul, MN (US)

(72) Inventors: Joannes F. H. M. Schuren, Linne (NL); Guido Hitschmann, Neuss (DE); Edward L. Weaver, II, Milford, OH (US); Kay Mohr, Sudlohn-Oeding (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 309 days.

(21) Appl. No.: 14/780,050

(22) PCT Filed: Mar. 19, 2014

(86) PCT No.: PCT/US2014/031220
§ 371 (c)(1),
(2) Date: Sep. 25, 2015

(87) PCT Pub. No.: WO2014/160572
PCT Pub. Date: Oct. 2, 2014

(65) Prior Publication Data
US 2016/0030251 A1 Feb. 4, 2016

(30) Foreign Application Priority Data

Mar. 27, 2013 (GB) .................................. 1305545.4

(51) Int. Cl.
*A61F 13/08* (2006.01)
*A61F 5/01* (2006.01)
*A61F 13/00* (2006.01)

(52) U.S. Cl.
CPC .......... *A61F 13/085* (2013.01); *A61F 5/0109* (2013.01); *A61F 13/00038* (2013.01)

(58) Field of Classification Search
CPC ...... A61F 13/08; A61F 13/085; A61F 5/0104; A61F 5/0111; A61F 13/06; A61F 13/062;
(Continued)

(56) References Cited

U.S. PATENT DOCUMENTS 3,845,769 A 11/1974 Shaw
5,254,122 A 10/1993 Shaw
(Continued)

FOREIGN PATENT DOCUMENTS

DE 4419287 12/1995
DE 202004010779 9/2004
(Continued)

OTHER PUBLICATIONS

International Search Report for PCT International Application No. PCT/US2014/031220 dated Aug. 11, 2014, 4 pages.

*Primary Examiner* — Ophelia A Hawthorne
(74) *Attorney, Agent, or Firm* — 3M Innovative Properties Company; Lynn R. Hunsberger

(57) ABSTRACT

A compression device for applying compression to a body part of a user. The compression device has a sleeve with two lateral side regions and a central region in-between. The central region of the sleeve comprises a main material having elasticity in at least a transverse direction. A maximum elongation in the transverse direction is from 5% up to and including 30% under a load of 10 N per cm width and a difference quotient of tension in the transverse direction from 20% elongation to 25% elongation equal to or greater that 0.6 N per cm width per percent elongation. The device further includes a releasable closure system configured and arranged relative to the sleeve, such that, in use, upon closure of the closure system the sleeve is restrained and tightened about the body part of the user.

13 Claims, 14 Drawing Sheets

(58) Field of Classification Search
CPC .... A61F 13/061; A61F 5/0109; A61F 13/107; A61F 5/0106; A61F 13/00038; Y10S 128/15
See application file for complete search history.

(56) References Cited

U.S. PATENT DOCUMENTS

| | | | |
|---|---|---|---|
| 5,916,183 | A | 6/1999 | Reid |
| 6,152,893 | A | 11/2000 | Pigg |
| 6,254,554 | B1 | 7/2001 | Turtzo |
| 6,338,723 | B1 | 1/2002 | Carpenter |
| 8,118,762 | B2 | 2/2012 | Bort |
| 8,758,282 | B2 | 6/2014 | Malhi |
| 2003/0060845 | A1 | 3/2003 | Gardon-Mollard |
| 2005/0113729 | A1 | 5/2005 | Scott |
| 2005/0192524 | A1 | 9/2005 | Lipshaw |
| 2005/0209545 | A1 | 9/2005 | Farrow |
| 2006/0135894 | A1 | 6/2006 | Linnane |
| 2007/0179421 | A1 | 8/2007 | Farrow |
| 2010/0004563 | A1 | 1/2010 | Lipshaw |
| 2010/0056973 | A1 | 3/2010 | Farrow |
| 2010/0312160 | A1 | 12/2010 | Creighton |
| 2011/0125183 | A1 | 5/2011 | Lipshaw |
| 2012/0078145 | A1 | 3/2012 | Malhi |

FOREIGN PATENT DOCUMENTS

| | | |
|---|---|---|
| EP | 1974704 | 10/2008 |
| JP | S54-142990 U | 10/1979 |
| JP | 2000-197654 A | 7/2000 |
| JP | 2000-508569 | 7/2000 |
| JP | 2001-245919 A | 9/2001 |
| JP | 2004-508101 A | 3/2004 |
| JP | 3123678 U | 7/2006 |
| JP | 2008-272042 A | 11/2008 |
| JP | 2012-071133 A | 4/2012 |
| WO | 97/39709 | 10/1997 |
| WO | WO 1997-046181 | 12/1997 |
| WO | WO 2001-72250 | 10/2001 |
| WO | WO 2009-139895 | 11/2009 |
| WO | WO 2010-117723 | 10/2010 |
| WO | WO 2011-066237 | 6/2011 |
| WO | WO 2012-003396 | 1/2012 |
| WO | WO 2012-021777 | 2/2012 |

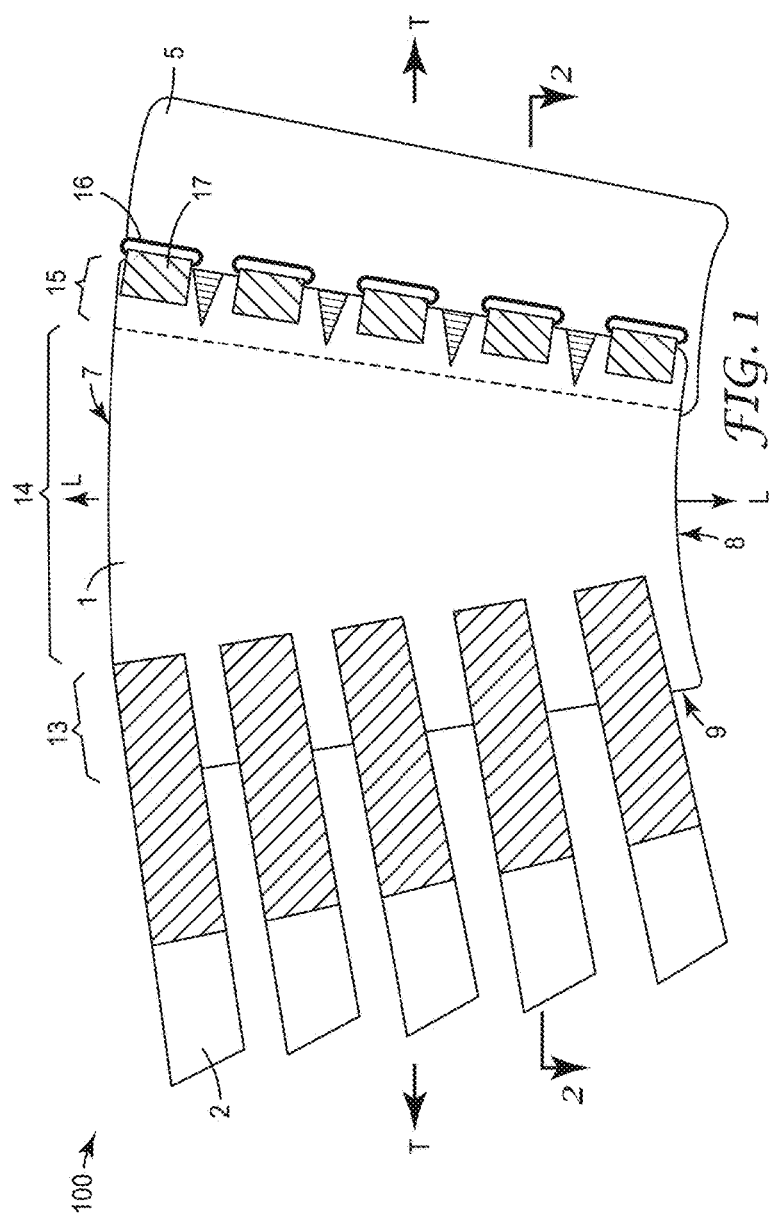

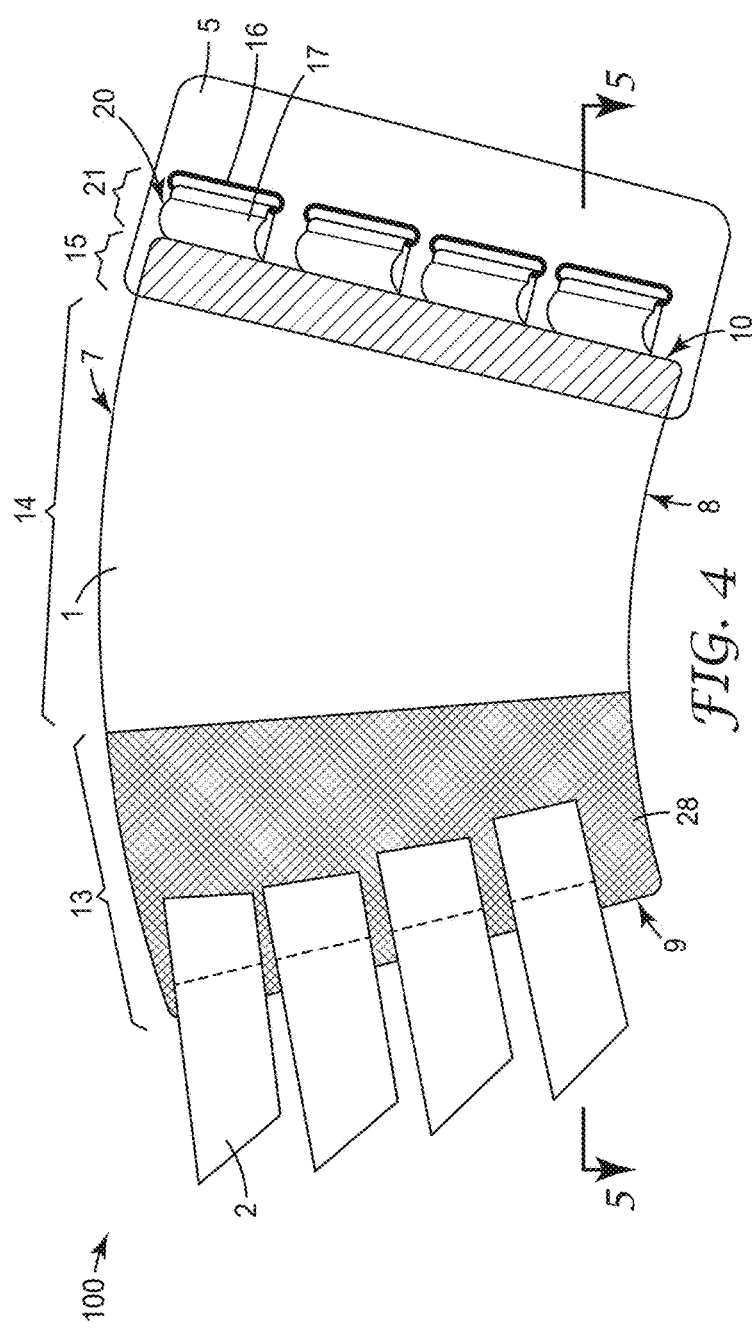
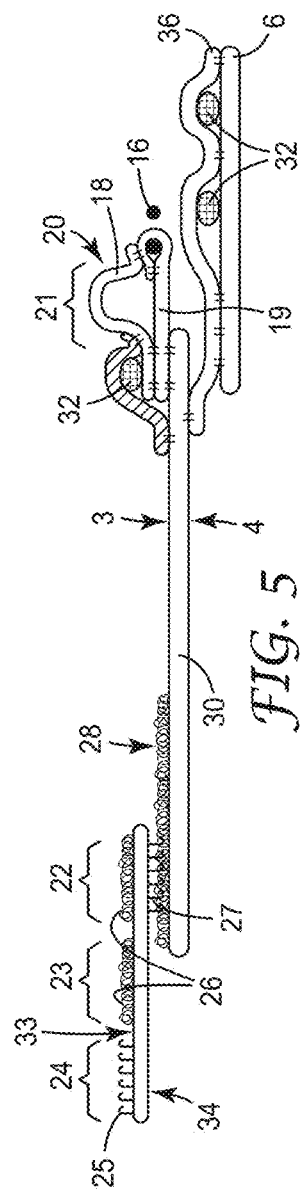

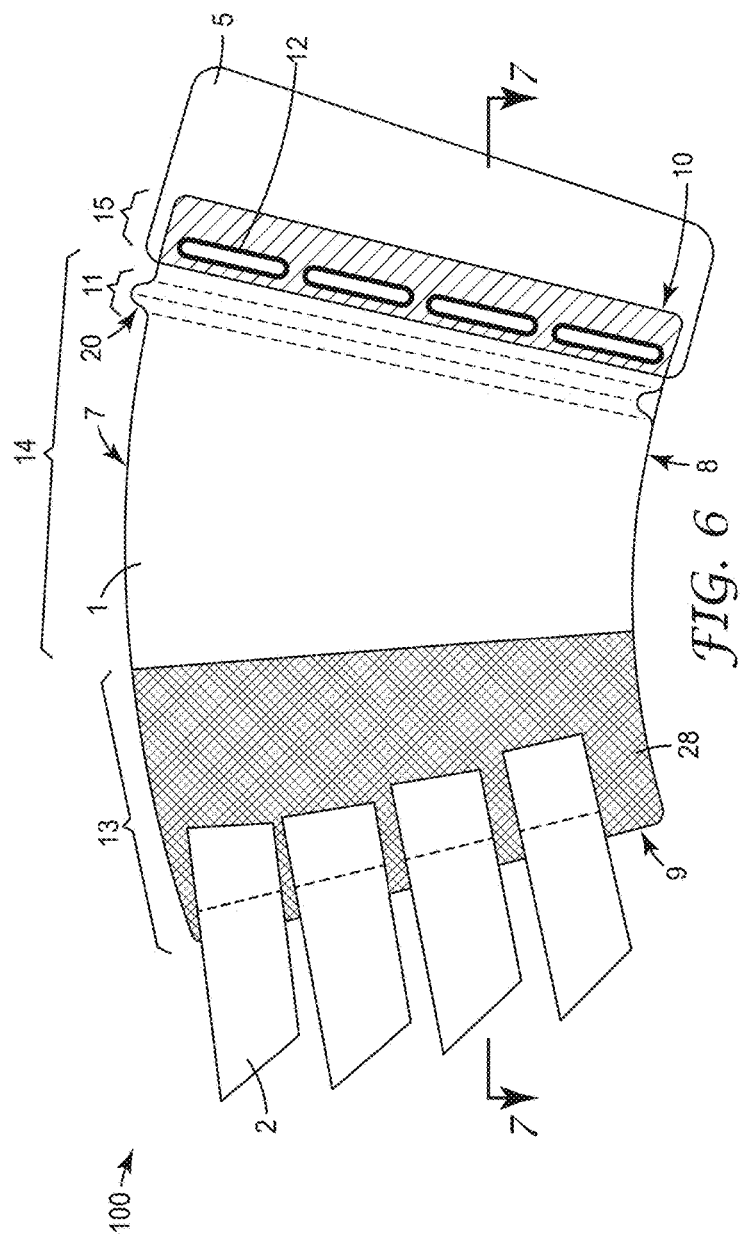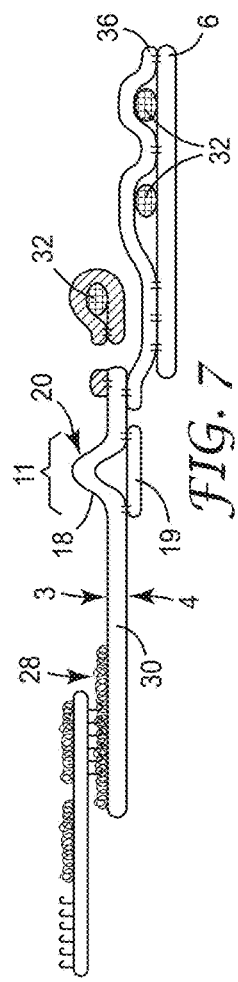

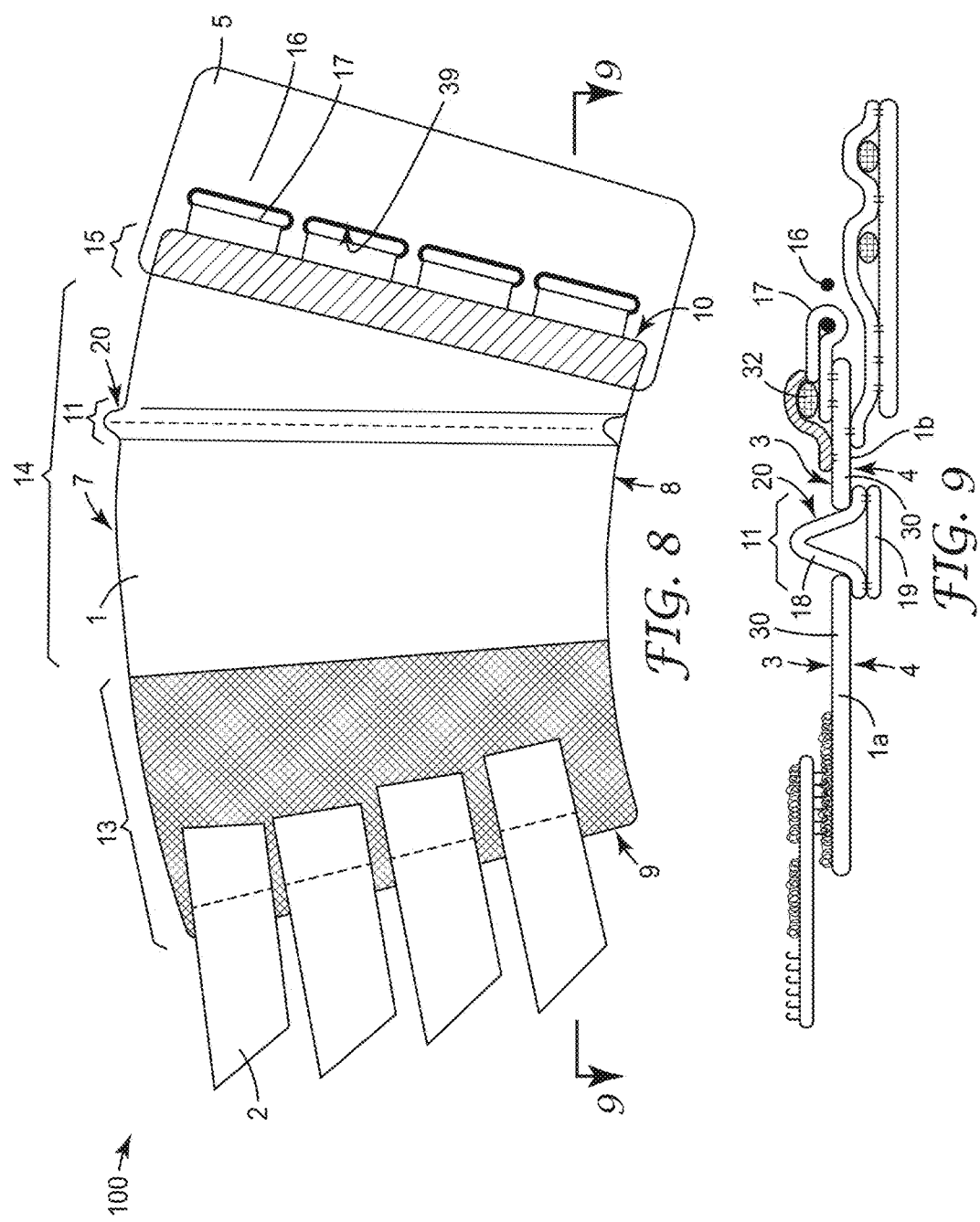

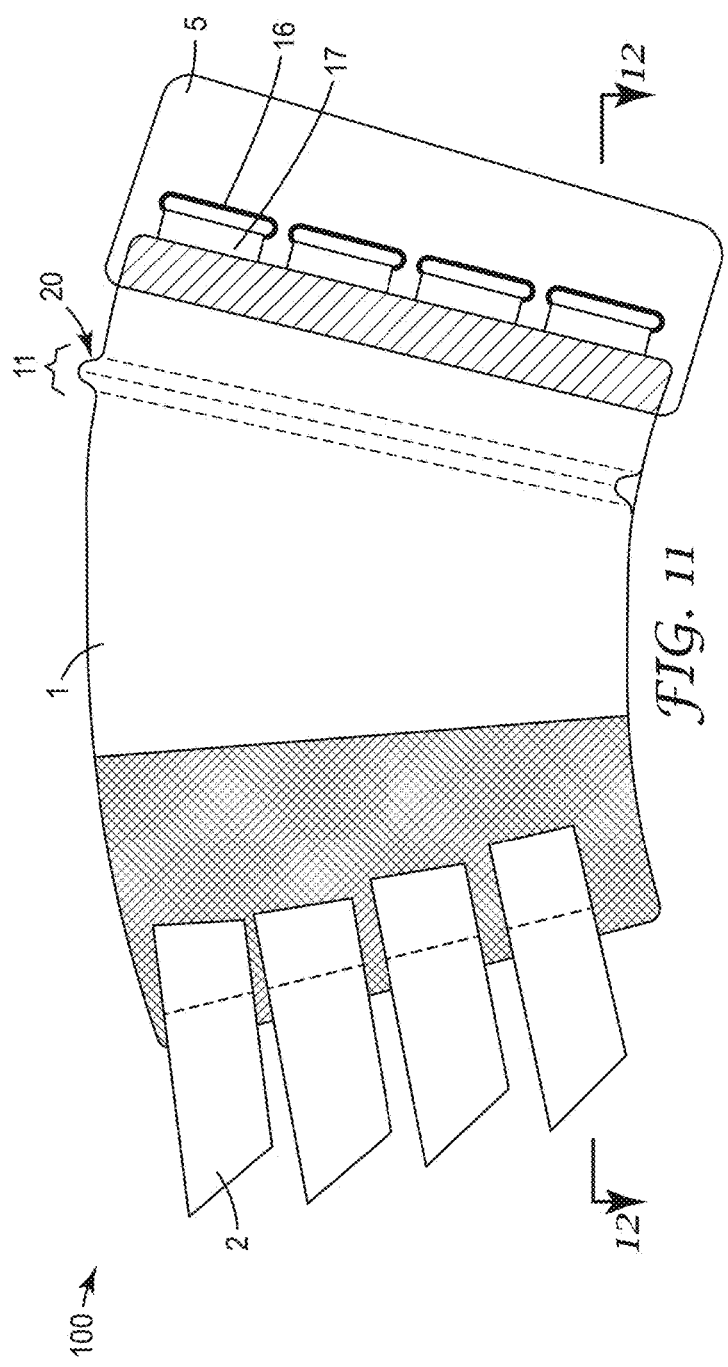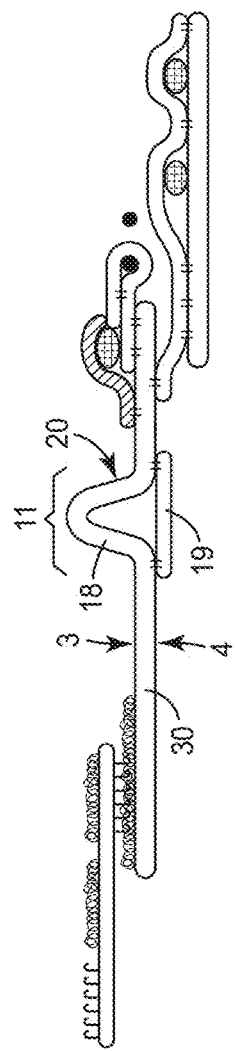

COMPRESSION DEVICE

CROSS REFERENCE TO RELATED APPLICATIONS

This application is a national stage filing under 35 U.S.C. 371 of PCT/US2014/031220, filed Mar. 19, 2014, which claims priority to Great Britain Application No. 1305545.4, filed Mar. 27, 2013, the disclosures of which are incorporated by reference in their entirety herein.

FIELD

The present disclosure relates to compression devices. In particular, the present disclosure relates to compression devices for applying compression to a body part (e.g. a limb, torso, neck or head) of a user for the use in the treatment and/or management of oedema and other venous and lymphatic disorders, more particularly venous leg ulcers and lymphoedema of a limb.

BACKGROUND

Compression therapy is generally prescribed to support an insufficient venous or lymphatic system in returning blood or lymph to the heart. Accordingly, compression is generally considered to be the standard treatment for use in the treatment of oedema and other venous and lymphatic disorders e.g. of the lower limbs venous leg ulcers and other clinical conditions, such as lymphoedema. The positive effects of compression therapy on venous lymph return, as well as on the healing of chronic venous (leg) ulcers, are well documented in the medical literature.

Compression bandages are one of the common compression systems used for compression therapy. The use of such compression bandages generally involves the application of a multilayer compression bandage. One concept behind a number of such multi-layer bandaging systems is the use of a combination of different types of bandage layers in order to apply pressure in layers (giving an accumulation of pressure) and to provide sustained compression together with rigidity. Commercially available compression bandages include bandages marketed under the trade designations "3M COBAN 2 LAYER COMPRESSION SYSTEM" and "3M COBAN 2 LITE COMPRESSION SYSTEM". Typically to assure proper and effective compression bandaging, it is normally necessary for a medical professional to apply the bandages. In consideration of the fact in the start of treatment of lymphoedema or in other compression therapies where oedema is present, compression bandages typically need to be replaced frequently due to changes in pressure (e.g. reduction of pressure) and/or in uniformity of pressure of the compression bandage as the amount of oedema is reduced during compression therapy, the need of having a medical professional change and reapply the compression bandage to ensure the desired pressure profile for continuing compression treatment can be limiting.

Compression stockings are often applied by users themselves. However, they often do not provide the desired therapeutic compressive pressure or are alternatively very hard to put on. Moreover, compression stockings need to be quite elastic showing high stretch so that one can pull them on and off. Such stockings retain this high stretch while being worn on the limb, and accordingly their effectiveness in terms of compression therapy is rather limited.

Other compression systems have been marketed and/or proposed. For example, U.S. Pat. No. 6,152,893 (Pigg et al; SMITH & NEPHEW) discloses a compression device for applying a predetermined compression to a limb comprising a pliable non-extensible sheet to be wrapped around a limb, where said sheet is provided with a plurality of cooperating first and second fastening parts each along opposing edges of the sheet, thereby to secure the device to the limb, wherein said first fastening part is provided with a plurality of first and second related indicia that visually indicate the relative movement of said first fastening part relative to said second fastening part between the application of zero tension as indicated by said first indicia and the application of a predetermined optimal degree of tension as indicated by said second indicia on fastening said first and second parts to provide compression. WO 01/72250 (Bennet et al; NEOPRESS) discloses an elastic compression support for supporting a wound dressing around the lower leg and foot of a patient, the support comprising a panel and a line of fastenings for drawing together two long edges of the panel where the fastenings comprise mutually aligned pairs of tapes secured to or tabs integral with the panel along its edges arranged so that drawing the tape or tabs apart in mutually opposite directions causes the panel to be tightened in compression around the limb, wherein the panel is formed from three pieces including a central piece, that lies at the back of the calf and under the foot, made of a long-stretch microperforated neoprene and two side pieces, that form the two long edges of panel and lie along the shin and the front of the leg, made of short-stretch microperforated neoprene. WO 97/46181 (Shaw et al; CIRCAID MEDICAL PRODUCTS) discloses a therapeutic compression garment including a plurality of pairs of body or limb encircle bands integrally connected to a central wrap around region and extending outwardly in opposite direction from the both sides of the central region to encompass the body part. WO 2011/066237 (Lipshaw et al; CIRCAID MEDICAL PRODUCTS) discloses a therapeutic compression garment, including: a body portion; and a spine portion, wherein the spine portion is releasably attached along a spine curve onto the body portion such that the spine portion is positionable at different locations on the body portion and wherein there are bands extending from either the body portion and/or the spine portion, the bands further securing the body and spine portions together when the body and spine portions are wrapped around a body limb. A corresponding garment is marketed by CIRCAID under the trade designation JUXTA-CURES which is formed from the body and spine portion between attached over a spine curve and includes four limb encircling bands (two per side, each including hook & loop type fasteners) integrally connected to both the body portion and the spine portion, the bands being located in staggered positions along the two opposite sides garment and extending outwardly in opposite directions from the both sides of the garment to encompass the body part. U.S. 2005/0209545 (Farrow et al; FARROW MEDICAL) discloses an apparatus for applying pressure to a body part comprising multiple interconnectable bands of compressible or non-compressible material and that the bands can be overlapped and connected to either via an spine or connective means lengthwise centrally in each band. A corresponding system is marketed by FARROW under the trade designation FARROWWRAP.

SUMMARY

While the aforementioned other compression systems may be, in part, easier to put on, it has been found that these systems still suffer a number of disadvantages, e.g. not providing desirable therapeutic compressive pressure and/or showing gaps, e.g. between bands or other open spaces (leading to undesirable area(s) of non-compression within a region undergoing compression and thus a unfavorable potential for fluid accumulation in said area(s)) and/or wrinkling and/or having narrow regions of overlap between regions of non-overlap (the latter two leading to non-uniform pressures, in particular areas of exceedingly high pressure).

Accordingly, there is an ongoing need or desire for a compression device that provides desirably effective compression therapy and is at the same time easy to put on and use, ideally without necessarily having a medical professional put it and/or change it each and every time.

We have found that it is particularly advantageous to provide a sleeve for substantially covering a portion of the body part (e.g. a limb, torso, neck, head) of a user where the sleeve is provided with closure system, such that in use upon closure of the closure system the sleeve is restrained and tightened about the body part of the user to provide compression (e.g. by drawing together the lateral side edges of sleeve), where the main material of the sleeve serving to provide compression has particular, select material properties. In this regard it has been found to be particular favorable to use a material having elasticity in the transverse direction of the sleeve together a maximum elongation from 5% to 30% under a load of 10 N per cm width in said transverse direction in conjunction with a difference quotient of tension in said transverse direction from 20% elongation to 25% elongation of at least 0.6 N per cm width per percent elongation.

Accordingly, there is disclosed a compression device for applying compression to a body part of a user comprising a sleeve for substantially covering a portion of the body part of a user, wherein the sleeve has an outer surface, an inner surface, an upper edge, a lower edge and two lateral side edges, wherein in the transverse direction from the first lateral side edge to the second lateral side edge the sleeve comprises a first lateral side region, a central region and a second lateral side region, and wherein at least the central region of the sleeve comprises a material (referred to in following as "main material") having elasticity in at least the transverse direction of the sleeve, a maximum elongation in said transverse direction from 5% up to and including 30% under a load of 10 N per cm width and a difference quotient of tension in transverse direction from 20% elongation to 25% elongation equal to or greater that 0.6 N per cm width per percent elongation; the device further comprising a releasable closure system, said closure system being configured and arranged relative to the sleeve, such that, in use, upon closure of the closure system the sleeve is restrained and tightened about the body part of the user.

For the sake of clarity, it is to be appreciated that after application of a compression device onto a body part (e.g. a limb, torso, neck or head) of a user, the transverse direction of the sleeve will also be a circumferential direction. In accordance with ASTM D4848-98 (2012) and BS EN 14704-1:2005 elasticity is that property of a material by virtue of which it tends to recover its original size and shape immediately after removal of the force causing deformation. Elongation as well as recovered elongation may be determined in accordance with the standard BS EN 14704-1:2005 "Determination of the elasticity of fabrics, —Part 1: Strip tests": Method A, Knitted Fabrics e.g. as described in detail below in the experimental section under the sub-section entitled "Test Methodology for Elongation and Recovered Elongation". Tension may be determined in accordance with the BS EN 14704-1:2005 "Determination of the elasticity of fabrics, —Part 1: Strip tests": Method A, Knitted Fabrics e.g. as described in detail below in the experimental section under the sub-section entitled "Test Methodology for Tension"

By employing in the sleeve a main material with very short stretch characteristics in conjunction with a relatively high (in other words steep) difference quotient of tension from 20% elongation to 25% elongation in said transverse direction, one can provide a compression device that provides desirably high standing pressures as a result of a high resistance to stretch, once applied. This has been found particular advantageous for effective compression therapy. Moreover, in one embodiment it is desirable to apply a compression device with stretching between about 10% to about 20% using a selected compression material having a steep difference quotient from 20% elongation to 25% elongation so that once applied the compression material resists any further stretching which in turns allow the attainment of high standing pressures.

In one embodiment, the difference quotient of tension in transverse direction from 20% elongation to 25% elongation is equal to or greater than 0.8 N per cm width per percent elongation, in one embodiment 1.0 N per cm width per percent elongation, in one embodiment equal to or greater than 1.2 N per cm width per percent elongation, in one embodiment equal to or greater than 1.4 N per cm width per percent elongation. In one embodiment, the difference quotient of tension in transverse direction from 20% elongation to 25% elongation equal to or less than 12 N per cm width per percent elongation, in one embodiment equal to or less than 10 N per cm width per percent elongation, in one embodiment equal to or less than 8 N per cm width per percent elongation, in one embodiment equal to or less than 6 N per cm width per percent elongation.

Main materials have a maximum elongation in said transverse direction from equal to or greater than 6% under a load of 10 N per cm width, in one embodiment equal to or greater than 7% under a load of 10 N per cm width. In one embodiment the main material has a maximum elongation in said transverse direction from equal to or less than 27% under a load of 10 N per cm width, in one embodiment equal to or less than 25% under a load of 10 N per cm width, in one embodiment equal to or less than 23% under a load of 10 N per cm width.

To facilitate comfort through e.g. lower supine (resting) pressures, main materials desirably have a difference quotient of tension in transverse direction from 15% elongation to 20% elongation that is shallower than the difference quotient of tension in transverse direction from 20% elongation to 25% elongation. In one embodiment, the difference quotient of tension in transverse direction from 15% elongation to 20% elongation is equal to or less than 70% of the difference quotient tension in transverse direction from 20% elongation to 25% elongation; in one embodiment equal to or less than 55% of the difference quotient tension in transverse direction from 20% elongation to 25% elongation, in one embodiment equal to or less than 45% of the difference quotient tension in transverse direction from 20% elongation to 25% elongation; in one embodiment equal to or less than 35% of the difference quotient tension in transverse direction from 20% elongation to 25% elongation.

To facilitate desirable contour fitting of compression devices, in particular sleeves thereof, desirably main materials have elasticity in the longitudinal direction of the sleeve. More desirably main materials show anisotropic elasticity characteristics where they are easier to stretch in the longitudinal direction. In one embodiment main materials have a ratio of tension in transverse direction at 30% elongation (or at 30% elongation after a one minute hold) to tension in longitudinal direction at 30% elongation (or at 30% elongation after a one minute hold) which is greater than 1.8, in one embodiment equal to or greater than 2.0, in one embodiment equal to or greater than 2.2.

In one embodiment, compression devices are configured and arranged such that the area of the central region is at least 40% (in particular at least 45%, more particularly at least 50%) of the total area of the sleeve. In addition or alternatively thereto, compression devices may be configured and arranged such that at a height corresponding to two-thirds the height of sleeve from the lower edge to the upper edge, the central region of the sleeve extends 40% or more across the sleeve in its transverse direction.

In one embodiment, at least 85% (in particular at least 90%, more particularly at least 95%) of the total area of the central region of the sleeve is made of said main material.

It is to be appreciated that since compressions devices, in particular the sleeves thereof will expand and/or change form in use, the aforesaid percent areas and width are relative to respective areas and width in the device when it is not in use. Further, it is to be appreciated that the sleeve, in particular the central region thereof, may comprise or be made of a single material having the corresponding properties of a main material or alternatively one or more materials each having the corresponding properties of a main material or alternatively one or more materials in the form of a composite material (e.g. laminate) said composite material having the corresponding properties of a main material.

As indicated above, compression devices described herein, in particular sleeves thereof, are particularly suited for covering a portion of a limb, a portion of the torso, a portion of the neck, a portion of a head or a portion of a neck and head in combination of a user e.g. for the use in the treatment and/or management of oedema.

For compression devices for applying compression to a limb, the sleeve may be configured and arranged to cover a limb such that the sleeve extends over at least one major muscle of the limb. For example, for compression devices designed for use on leg, said at least major muscle may be selected from the following: tibialis anterior, soleus, gastrocnemius, bicep femoris, rectus femoris, vastus medialis, vastus intermedius, vastus lateralis. It will be appreciated the first three listed muscles are major muscles in the lower leg, while the latter five are major muscles in the upper leg (the last four forming the muscle group called quadriceps femoris). Compression devices may be designed for use on just the lower leg or just the upper leg, or alternatively for both the lower and upper leg. It will also be appreciated that typically a combination of major muscles will be covered. For compression devices designed for use on arm, said at least major muscle may be selected from the following: flexor carpi radialis, flexor carpi ulnaris, palmaris longus, brachioradialis, biceps brachii, triceps brachii, brachialis. It will be appreciated that the first four listed muscles are major muscles in the lower arm, while the latter three are major muscles in the upper arm, and that the compression devices may be designed for use just on the lower arm or upper arm or alternatively for both the lower and upper arm. Again it will also be appreciated that typically a combination of major muscles will be covered.

The dependent claims define further embodiments of the invention.

It is to be understood that the present invention covers all combinations of particular, suitable, desirable, favorable advantageous and preferred aspects of the invention described herein.

BRIEF DESCRIPTION OF DRAWINGS

The invention will now be described with reference to the accompanying drawings in which:

FIG. 1 represents a top view of an exemplary embodiment of a compression device described herein, while FIG. 2 shows a cross-sectional view of the exemplary embodiment depicted in FIG. 1.

FIG. 3a represents a perspective, front view of the exemplary embodiment depicted in FIGS. 1 and 2 shown in use on the lower leg of a user, while

FIG. 4 represents a top view of another exemplary embodiment of a compression device described herein, while FIG. 5 shows a cross-sectional view of the exemplary embodiment depicted in FIG. 4.

FIG. 6 represents a top view of a further exemplary embodiment of a compression device described herein, while FIG. 7 shows a cross-sectional view of the exemplary embodiment in FIG. 6.

FIG. 8 represents a top view of yet another exemplary embodiment of a compression device described herein, while FIG. 9 shows a cross-sectional view of the exemplary embodiment in FIG. 8.

FIG. 11 represents a top view of an additional exemplary embodiment of a compression device described herein, while FIG. 12 shows a cross-sectional view of the exemplary embodiment in FIG. 11.

FIG. 13 represents a top view of prototype construction used for testing, while

FIG. 15 b and c show the outer surface of the other side (side 2)

FIG. 16 a to d show SEM images of the warp knitted spacer fabric marketed by Müller Textil, 51674 Wiehl, Germany under the trade designation 3 Mesh 5992 (M2), where

Figure 3A:
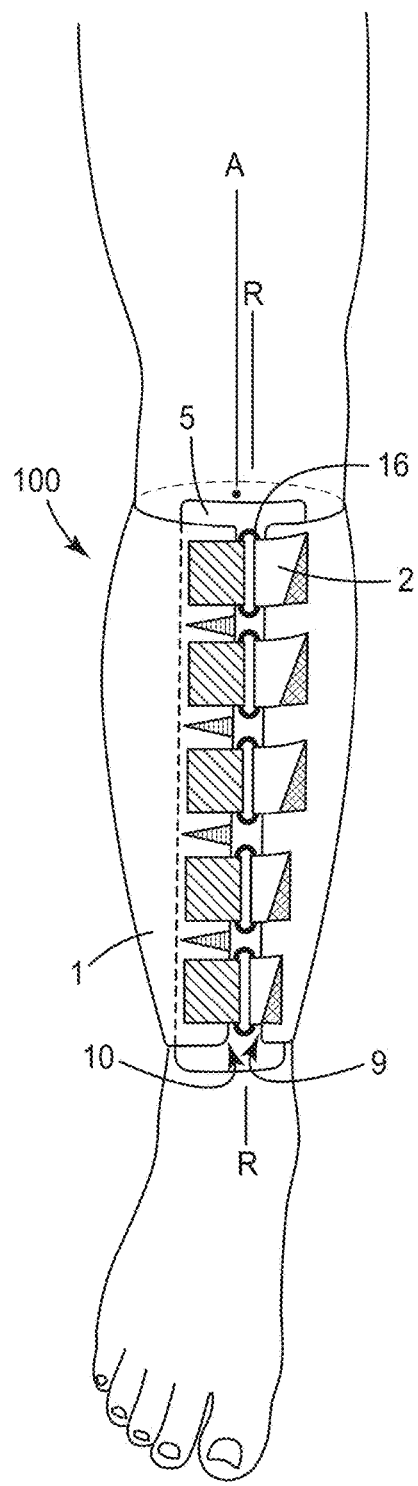
Figure 3B:
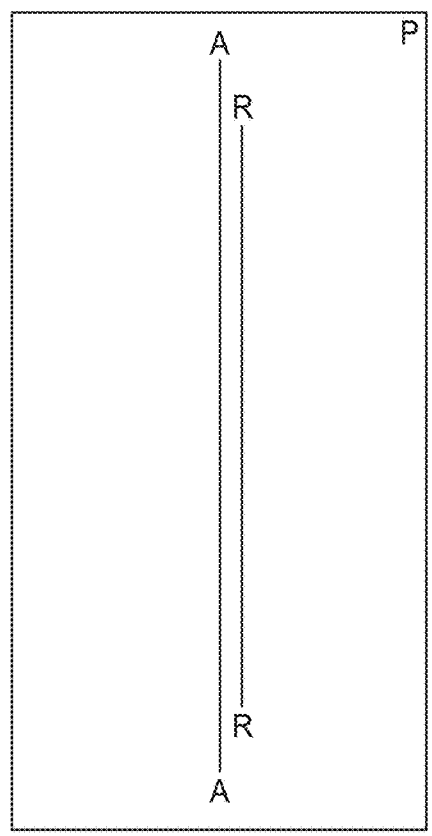
FIG. 3b shows a projection of the axis R (which is depicted in FIG. 3a) onto a plane P containing the central axis A (that is also depicted in FIG. 3a).

In the description that follows, unless expressly stated otherwise, terms such as 'top', 'bottom', 'above', 'below', etc, refer only to features as shown in the Figures, and no restriction as to orientation of use, etc, is intended. Not all Figures are to the same scale.

DETAILED DESCRIPTION

It is to be understood that the present invention covers all combinations of particular, suitable, desirable, favorable, advantageous and preferred aspects of the invention described herein.

FIG. 1 shows a top view of the exterior of an exemplary embodiment of a compression device (100) for use in applying compression to a body part, in particular a limb of a user, while FIG. 2 shows a cross-sectional view of this exemplary embodiment. The device comprises a sleeve (1) for substantially covering a portion of the body part, in particular a portion of the limb of a user. The sleeve includes an outer surface (3), an inner surface (4), an upper edge (7) and a lower edge (8). When the device is in use on the limb, typically the inner surface (4) is located towards the wearer/user. (In the following the term "inner" will typically refer to something located towards the wearer/user and "outer" away from the wearer/user. For compression devices for use in applying compression to a limb, the upper edge will typically be located towards the torso of the user and the lower edge distant to the torso of the user, and for compression device for use in applying compression to the torso, neck or head, the upper edge will typically be located distant to the legs and the lower edge towards the legs, and both upper and lower edges, being essentially transverse, will generally be located essentially circumferentially around the relevant body part after application.) As mentioned above, after application of a compression device onto a body part (e.g. a limb) of a user, the transverse direction of the sleeve will also be a circumferential direction. In FIG. 1, the transverse direction of the sleeve is indicated by the symbols: T←→T, while the longitudinal direction of the sleeve is indicated by the symbols: L←→L. As can be appreciated from FIG. 1, the sleeve includes two lateral side edges (9, 10) extending from its upper edge to its lower edge. In the transverse direction of the sleeve (from the first lateral side edge (9) to the second lateral side edge (10) the sleeve comprises a first lateral side region (13), a central region (14) and a second lateral side region (15).

Sleeves, when laid out flat (e.g. as depicted in FIG. 1) may be substantially rectangular, trapezoidal or irregular in shape. For example, the sleeves in a number of exemplary embodiments depicted herein (e.g. in FIG. 1) are substantially trapezoidal in shape. For facilitating an optimal fit onto a part of the body (e.g. a limb, torso, neck or head) of a user, the upper edge and/or the lower edge of the sleeve may be favorably slightly curved, in particular the upper edge may be slightly convex and/or the lower edge may be either slightly concave or convex. Alternatively or in addition thereto, one or both of the lateral side edges may be slightly curved, in particular slightly convex. This may be facilitating fitting over well-developed calves. In use, when the compression device is applied onto a body part (e.g. a limb, torso, neck or head) of the user, favorably the sleeve is substantially cylindrical, barrel or truncated-conical in shape.

Compression devices described herein further comprise a releasable closure system. The closure system is configured and arranged relative to the sleeve, such that, in use, upon closure of the closure system the sleeve is restrained and tightened about the body part (e.g. limb, torso, neck or head) of the user. Desirably the sleeve and closure system are configured and arranged such that in use, upon closure of the closure system, the two lateral edges of the sleeve are drawn towards one another, but do not overlap.

Releasable closure systems may include zippers, e.g. wherein the first lateral edge of the sleeve may be provided with one half of said zipper and the second lateral edge is provided with a complementary half of said zipper. The term "zipper" as used herein includes mechanical closure devices comprising two zipper-tape halves, each provided teeth or other elements including (e.g. male and/or female) interlocking profiles, which can interlocked together or disengaged from another via the use of a slider to form a closed or opened zipper chain, respectively. An example of a toothless zipper includes the closure system marketed by GORE under the trade designation LOCKOUT which includes a slider that interlocks the two double channeled polymer tracks.

Desirably releasable closure systems allow for individualized tighten along the longitudinal direction of the sleeve. Examples of such systems may include closure systems comprising a plurality of opposing lace guides provided on the outer surface of two lateral side regions of the sleeve and a lace extending back and forth between the opposed guides. Such closure systems may further comprise at least one rotatable tightening mechanism configured to apply tension on the lace thereby advancing the opposed guides towards each other. In particular the at least one rotatable tightening mechanism may be integrally formed with at least one guide. Typically in such reel-lacing systems the lace has no free end. Other examples of such releasable closure systems may comprise a mechanical fastening closure system.

For example, the first lateral region or the second lateral region or both regions may be provided with a plurality of tabs, wherein each tab comprises a proximal end portion and a distal end portion, said proximal end portion being releasably or fixedly attached to the first lateral edge region and/or second lateral edge region of sleeve, respectively, such that the tab extends across the first lateral side edge and/or the second lateral side edge, respectively, in substantially the transverse direction of the sleeve, with its distal end portion positioned away from the central portion of the sleeve. The inner major surface (i.e. that surface of the tab facing towards the wearer) of each tab at the distal end portion of the tab may then comprise one part of a mechanical fastening system (e.g. hook, stem and/or cup-shaped fasteners). At least outer surface at the second and/or first lateral edge region, respectively, opposite to each tab may then comprise the complementary part of the mechanical fastening system (e.g. said outer surface may have a structure or be provided with a structure that is adapted to be engaged by said fasteners). Such tabs may have a width relative to the transverse direction of the sleeve of at least 6 cm. Such tabs may have a width relative to the transverse direction of the sleeve of at most 25 cm. Such tabs may have a height relative to the transverse direction of the sleeve of at least 1 cm, in particular at least 2 cm, more particularly at least 3 cm. Such tabs may have a height relative to the transverse direction of the sleeve of at most 10 cm, in particular at most 8 cm, more particular at most 6 cm.

As mentioned above the proximal end of such tabs may be either fixedly or releasably attached to the respective first and/or second lateral side region of the sleeve. When such tabs are releasably attached, inner major surface at the proximal end portion of the tabs may be provided with hook, stem and/or cup-shaped fasteners (second tab fasteners) and the outer surface of the first and/or second lateral edge region of the sleeve may have a structure or be provided with a structure that is adapted to be engaged by said second tab fasteners.

Accordingly the inner major surface at the proximal end portion of the fastening tabs may be then releasably attached to the outer surface of first and/or lateral edge region of the sleeve, respectively. The second tab fasteners may be identical to the first tab fasteners or different. In the event that the second and first tab fasteners are different, favorably the outer surface at the first and second lateral edge regions of the sleeve have a structure or are provided with a structure that is adapted to be engaged by both the first and second fasteners.

Another example of a releasable closure system comprise a mechanical fastening closure system and favorably allow for individualized tighten along the longitudinal direction of the sleeve includes systems including fastening tabs in conjunction with rings or eyelets. For example the second lateral edge region of the sleeve may be provided with either a plurality of eyelets or a plurality of rings in series between the upper and lower edges of the sleeve. The device may then further comprise a plurality of strip-shaped mechanical fastening tabs, wherein a single fastening tab is provided for each eyelet or ring, as applicable, each fastening tab comprising a proximal end portion and a distal end portion being connected by an inner tab portion, wherein said proximal end portion is releasably or fixedly attached to the first lateral edge region of sleeve such that the fastening tab is located opposite to an eyelet or ring, as applicable, and extends in substantially the transverse direction of the sleeve with its distal end portion positioned away from the central portion of the sleeve, wherein the outer major surface at the distal end portion of the fastening tab comprises one part of a mechanical fastening system and said outer major surface at the proximal end portion of the fastening tab comprise the complementary part of the mechanical fastening system. Such fastening tabs and eyelets or rings, as applicable, are configured and arranged such that, in use, the tabs are passed through the eyelets or rings, as applicable, then turned back on themselves such that the first lateral side edge of the sleeve is drawn towards the eyelets or rings, as applicable, and then fastened so that the sleeve is tightened and restrained about the body part (e.g. limb, torso, neck or head) of the user. The exemplary embodiment shown in FIGS. 1 and 2 as well as other exemplary embodiments discussed herein include such a releasable closure system.

Returning to the exemplary embodiment of FIGS. 1 and 2, it can be seen that the second lateral edge region (15) of the sleeve (1) is provided with a plurality of rings (16) (for ease in viewing only one ring is labelled with the reference number) in series between the upper and lower edges of the sleeve. Each ring is attached, in this particular exemplary embodiment fixedly attached by a strap (17) to the sleeve; the straps extending in the transverse direction. The ring straps may be directly attached to the sleeve or alternatively via an intermediate connecting element. In this particular exemplary embodiment, the straps are connected to an intermediate elongate, castellated element (17a) that is directly attached to sleeve, in particular onto the outer surface (3) of the sleeve at the second lateral side region. It will be appreciated that although in this exemplary embodiment, the rings and straps are fixedly attached, in alternative embodiments straps they could be releasably attached. The exemplary compression device (100) further comprises a plurality of strip-shaped mechanical fastening tabs (2) (again for ease in viewing only one fastening tab is labelled). There is a single tab provided for each ring (16). Each tab comprises a proximal end portion (22) and a distal end portion (24) being connected by an inner tab portion (23). In this exemplary embodiment, the proximal end portion (22) is attached e.g. via adhesive, bonding, or stitching) to the first lateral edge region (13) of sleeve (1). It is to be appreciated that the proximal end portion could alternatively being releasably attached to the first lateral edge region of the sleeve (for example as illustrated in other exemplary embodiments described herein). The fastening tabs (2) are attached onto the sleeve such that there is a tab located opposite to a ring and such that each tab extends in substantially the transverse direction of the sleeve, with its distal end portion (24) positioned away from the central portion of the sleeve. From FIG. 2, it can be seen that each tab has a first major surface, i.e. an inner major surface (34), located towards the outer surface (3) of the sleeve and a second major surface, i.e. an outer major surface (33), located away from the outer surface of the sleeve. The outer major surface (33) at the distal end portion (24) of the tab comprises one part (25) of a mechanical fastening system and said second major surface at the proximal end portion of the tab comprises the complementary part (26) of the mechanical fastening system. As can be seen in this exemplary embodiment shown in FIGS. 1 and 2 and the other exemplary embodiments described herein, the second major surface at the inner tab portion of the fastening tab may also comprise the complementary part (26) of the mechanical fastening system.

Referring to FIG. 3a showing a perspective, front view of the exemplary compression device (100) depicted in FIGS. 1 and 2, in use on the lower leg of a user, it can be recognized that the fastening tabs (2) and rings (16) are configured and arranged such that, in use, the fastening tabs are passed through the rings, turned back on themselves such that the first lateral side edge (9) of the sleeve (1) is drawn towards the rings and finally fastened so that the sleeve is tightened and restrained about the limb of the user to provide compression. Once positioned onto the limb of the user, the compression device (100) advantageously encircles the relevant portion of the limb and, in this exemplary embodiment the sleeve (1) and in particular the central region (14) of the sleeve will encircle most of the limb.

In general, such fastening tabs (i.e. fastening tabs that are turned back on themselves during fastening) are favorably configured such that the second major surface at the distal end portion of the fastening tabs is provided with hook, stem and/or cup-shaped fasteners (first tab fasteners) and the second major surface at the proximal end portion of the fastening tabs has a structure or is provided with a structure that is adapted to be engaged by said first tab fasteners.

The second major surface at the inner portion of the fastening tabs may also have a structure or be provided with a structure that is adapted to be engaged by the first tab fasteners. Favorably such fastening tabs are attached to the first lateral side region such that the fastening tabs extend across the first lateral side edge, in particular the fastening tabs extend at least 2 cm outwardly beyond said side edge.

For embodiments including a plurality of eyelets or rings, as applicable, favorably the interstices between eyelets or rings, respectively, extends over a height corresponding to at least 70% of the height of the sleeve from the upper to lower edge. The height of the interstices between eyelets and rings, as applicable, may range from 0.1 mm to 7 cm, inclusive, in particular from 0.3 mm to 3 cm, inclusive, and more particular from 0.5 mm to 2 cm.

As will be appreciated from the exemplary embodiment shown in FIGS. 1 and 2 and the other exemplary embodiments described herein, to facilitate application and an overall smooth fit of the device, eyelets and rings, as applicable, are favorably configured and/or selected, such that the opening of the eyelet or ring has a height relative to the transverse direction of the sleeve which is greater than the height relative to the transverse direction of the sleeve of the fastening tab. And for those embodiments including rings and straps, favorably the rings are configured and/or selected, such that the opening of the ring has a height relative to the transverse direction of the sleeve which is greater than the height relative to the transverse direction of the sleeve of the strap. In addition or alternatively, eyelets and rings, as applicable, are desirably rectangular or substantially rectangular in form; or oval or substantially oval in form (e.g. narrow or elongate oval, canoe-form, elongate teardrop); or a elongate or narrow D-shape in form. Rings are favorably positioned along the (first or second) lateral edge of the sleeve either adjacent to or spaced apart from said edge and away from the (first or second) lateral edge portion, in particular wherein each ring has a lateral edge near the (first or second) lateral edge of the sleeve, said lateral edge of the ring is either positioned adjacent to (first or second) lateral edge of the sleeve or spaced apart from the (first of second) second lateral edge at a distance of at most 4 cm, in particular at most 3 cm.

Fastening tabs desirably have a height relative to the transverse direction of the sleeve of at least 1 cm, more favorably as least 2 cm. more desirably at least 3 cm. Fastening tabs desirably have a height relative to the transverse direction of the sleeve of at most 10 cm, more desirably at most 8 cm, most desirably at most 6 cm. Fastening tabs desirably have a width relative to the transverse direction of the sleeve of at least 6 cm. Fastening tabs desirable have a width relative to the transverse direction of the sleeve is at most 25 cm.

Straps desirably have a height relative to the transverse direction of the sleeve of at least 1 cm, more desirably at least 2 cm, most desirably at least 3 cm. Desirably straps have a height relative to the transverse direction of the sleeve of at most 10 cm, more favorably at most 8 cm, most favorably at most 6 cm. The height of the interstices between straps may range from 0.3 mm to 7 cm, inclusive, in particular from 0.3 mm to 3 cm, inclusive, and more particular from 0.5 mm to 2 cm.

As it can be appreciated from exemplary embodiment shown in FIGS. 1 to 3a, it may be desirable to configure and arrange the sleeve, eyelets or rings, as applicable, and fastening tabs, such that in use, when the fastening tabs are passed through the eyelets or rings, as applicable, turned back and fastened onto themselves, the first lateral edge is drawn towards the second lateral edge of the sleeve, but the two lateral edges of the sleeve do not overlap. Also as it can be appreciated from the exemplary embodiment shown in FIGS. 1 to 3a, compression devices may further comprise a tongue. The tongue is desirably configured and arranged relative to the sleeve such that, in use, the tongue is generally centrally positioned adjacent to and extends along the first and second lateral edges of the sleeve, so that the tongue is located between the user and an opening defined between the first and second lateral edges of the sleeve and so that the tongue underlies at least a portion (typically that portion adjacent to the first and second lateral edges) of each the first and second lateral side regions.

For compression devices including a tongue, the tongue may comprise foam, in particular memory foam, more particular high density memory foam. High density memory foams are memory foams that have a density of at least 65 kg/m$^3$, in particular at least 70 kg/m$^3$, more particularly at least 85 kg/m$^3$, most particularly at least 105 kg/m$^3$. Examples of suitable memory foams include high density memory foams available from Filtrona Porous Technologies marketed under the trade designations SRF EP2, Argus, Argus Soft, and Argus Supersoft. Favorably the tongue comprises one or more layers of foam, in particular a layer of foam having a thickness from 0.5 mm to 10 mm, inclusive, more particular a layer of foam having a thickness from 2 mm to 6 mm, inclusive. Alternatively or in addition, tongues may favorably include a stiffener, e.g. in the form of elongate wires, bars, grids, or pads. Tongues may include either a single stiffener extending substantially across its width and length or one or more stiffeners extending lengthwise provided in series across the width of the tongue.

Compression devices, in particular sleeves, more particularly the first and/or second lateral side regions thereof, may also be provided with one or more stiffeners to facilitate maintenance of sleeve shape, in particular to minimize any tendency towards vertical collapsing or slipping-down of the sleeve, stiffeners may be provided e.g. in the form of wires, bars, grids, or pads having limited width relative to the transverse direction of the sleeve. In the exemplary embodiment depicted in FIGS. 1 and 2, for example, an elongate stiffener (32) that extends lengthwise between the upper and lower edges of the sleeve is provided in the second lateral side region (15) adjacent to the second lateral edge (10).

Stiffeners may be made of e.g. metal or thermoplastic materials including thermoformable thermoplastic materials (such as polypropylene, polyamide, polyester (e.g. 3M Scotchcast Thermoplastic Material 72362)). For stiffeners having a width greater than five millimeters, it may be favorable to provide them with perforations to allow for breathability. For design and/or fixing purposes, stiffeners may be provided within a fabric pocket which is subsequently attached to the appropriate part(s) of the sleeve or tongue, as the case may be; or alternatively stiffeners may be positioned on the surface of the appropriate part(s) of the sleeve or tongue, as applicable, which are then covered completely with a sheet of fabric that is sewn or laminated onto the respective part(s) of the sleeve or tongue, as applicable.

Returning to the exemplary embodiment depicted in FIGS. 1 and 2, it can be seen that elongate stiffener (32) that extends lengthwise between the upper and lower edges of the sleeve is provided in the second lateral side region (15) adjacent to the second lateral edge (10). The stiffener is covered with a piece of fabric (32a). It can also be seen that the exemplary compression device (100) includes a tongue (5). The tongue, in particular a lateral edge portion thereof, is affixed to the inner surface (4) at the second lateral edge region (15) of the sleeve so that the tongue extends beyond the second lateral edge (10) and underlies the rings (16). Referring to FIG. 3a, it can be recognized that the sleeve (1) and fastening tabs (2) of the exemplary compression device (100), are configured and arranged, such that in use, when the fastening tabs are passed through the eyelets or rings, as applicable, turned back and fastened onto themselves, the first lateral edge (9) is drawn towards the second lateral edge (10) of the sleeve, but the two lateral edges of the sleeve do not overlap. In addition it can be seen in FIG. 3a, that when the compression device (100) is in use on the body part, here the limb, of the user, the tongue (5) is generally centrally positioned adjacent to and extends along the first and second lateral edges (9, 10) of the sleeve (1), so that the tongue is located between the user and an opening defined between the first and second lateral edges of the sleeve underlying at least in part the first and second lateral edge regions. Also it can be recognized in FIG. 3a, that when the exemplary compression device (100) is in use on the limb of the user, the sleeve is disposed about a central axis (A) and the plurality of rings extends along a second axis (R). Making reference to FIG. 3b it can be seen that relative to a projection of the second axis (R) onto said plane (P) containing the central axis (A), the second axis (R) is in parallel or essentially parallel alignment relative to the central axis.

For those embodiments including a plurality of rings or eyelets, when in use on the body part (e.g. limb, torso, neck or head) of the user, the sleeve will be disposed about a central axis (A), said central axis lying in a plane (P), and the plurality of rings or eyelets extends along a second axis (R), wherein relative to a projection of the second axis (R) onto said plane (P) containing the central axis (A), the second axis is either in parallel alignment relative to the central axis or nearly parallel alignment relative to the central axis (i.e. the second axis (R) may be inclined forming an acute angle of no more than 5° relative to the central axis). It is to be appreciated that when the compression device is in use on the body part of the user, it is possible that the series of rings or eyelets may not extend along a perfectly straight axis, i.e. its projection may be curved due to tension and particular geometry of the relevant body part of the user, and in such cases the relevant axis along which the series of rings extends may be defined as being the axis resulting from a best linear fit (linear regression) to the projected curve.

As can be appreciated from FIG. 3a, for compression devices suitable for use with the lower leg of the user, favorably the sleeve is configured and arranged such that in use the rings, or for those embodiments having eyelets, the eyelets, will generally be positioned towards the front, in particular so that they extends generally along the tibia. Accordingly for such embodiments the central region of the sleeve will typically be positioned around the back and, at least on one of the sides of the lower leg, and thus accordingly next to the calf muscles.

Compression devices described herein are particularly useful for applying compression to a limb. Desirably the sleeve is configured and arranged to cover a limb such that the sleeve extends over at least one major muscle of the limb. For example, for compression devices designed for use on a leg (e.g. the lower leg and/or the upper leg), said at least major muscle may be appropriately selected from the following: tibialis anterior, soleus, gastrocnemius, bicep femoris, rectus femoris, vastus medialis, vastus intermedius and vastus lateralis; while for compression devices designed for use on an arm (e.g. the lower arm and/or the upper arm) said at least major muscle may be appropriately selected from the following: flexor carpi radialis, flexor carpi ulnaris, palmaris longus, brachioradialis, biceps brachii, triceps brachii, and brachialis. As mentioned previously, typically a combination of major muscles will be covered.

Compression devices described herein, in particular the sleeves thereof, can be provided in different sizes to accommodate the difference in the size of body parts (e.g. limbs versus torsos or necks or heads; or e.g. relative to just limbs, arms versus legs) as well as the general difference in sizes of a particular body part. Compression devices suitable for use with necks and heads will often be used for both, i.e. configured to cover a portion of both the neck and head of the user. Such devices may be configured for example like a hood covering the neck, chin and over the head leaving the face free where the releasable closure system may be provided either along the top and back of the head or along the front down the chin and front of the neck.

Compression devices described herein are particularly suitable for use on limbs, in particular the lower leg including the calf (e.g. for treating among other things venous leg ulcers and lymphoedema of the leg). In regard to the latter, for example considering the size of an adult human lower leg, including those persons suffering from lymphodema, can range from around 130 to 420 mm in circumference at the ankle and around from 280 to 650 mm in circumference at their widest point, it could be possible to provide compression devices in for example seven standard (width) sizes, e.g. XS, S; M, L, XL, XXL, XXXL, aimed to cover 80% of the potential relevant circumferential sizes of the potential users while the remaining 20% could be provided for by special order. In addition, considering the length of an adult human lower leg can range from around 20 cm to 40 cm, it could be possible to provide in conjunction with the standard (width) sizes mentioned above, three height sizes, e.g. short, average and, tall, again aimed to cover 80% of the potential relevant lengths of the potential users. In regard to the standard width sizes, the number of standard sizes to cover 80% the potential relevant circumferential sizes of the potential users could be reduced by for example providing compression devices configured such that the width of the sleeve could be readily adjusted by the user or the care-giver applying the compression device onto the limb of the user. In particular, it would be advantageous to provide compression devices wherein the fastening tabs is releasably attachable to the first lateral edge region of the sleeve as described herein and wherein the first lateral edge region of the sleeve is configured such that it is trimmable. The exemplary embodiments depicted in FIGS. 4 to 12 and discussed in more detail provide examples of such compression devices.

From FIG. 2, it will be noted that the three regions (13, 14, and 15) of the sleeve comprise the same material (30). This material is the main material. Further it should be appreciated due to the attachment of a stiffener (32), the ring-straps (17) and tongue (5) to the sleeve at the second lateral side region (15) and the attachment of fastening tabs (2) at the first lateral side region (13), the properties of the underlying main material (30) in these two regions will normally be affected. Moreover typically the maximum elongation in the transverse direction under a load of 10 N per cm of the first and/or second lateral side regions will be lower (most often significantly lower approaching and possibly reaching 0% elongation) than the maximum elongation in the transverse direction under a load of 10 N per cm of the central region of the sleeve. Finally it will be appreciated that in the central region of the sleeve, this region being free of such attachments, the properties of the main material remain unaffected.

As indicated above, at least the central region of the sleeve comprises a material (i.e. main material) having elasticity in at least the transverse direction of the sleeve, a maximum elongation in said transverse direction from 5% up to and including 30% under a load of 10 N per cm width, a difference quotient of tension in transverse direction from 20% elongation to 25% elongation equal to or greater than 0.6 N per cm width per percent elongation.

In one embodiment, the difference quotient of tension in transverse direction from 20% elongation to 25% elongation is equal to or greater than 0.8 N per cm width per percent elongation, in one embodiment 1.0 N per cm width per percent elongation, in one embodiment equal to or greater than 1.2 N per cm width per percent elongation, in one embodiment to or greater than 1.4 N per cm width per percent elongation. In one embodiment, the difference quotient of tension in transverse direction from 20% elongation to 25% elongation equal to or less than 12 N per cm width per percent elongation, in one embodiment equal to or less than 10 N per cm width per percent elongation, in one embodiment equal to or less than 8 N per cm width per percent elongation, most favorably equal to or less than 6 N per cm width per percent elongation.

In one embodiment, main materials have a maximum elongation in said transverse direction from equal to or greater than 6% under a load of 10 N per cm width, in one embodiment equal to or greater than 7% under a load of 10 N per cm width. In one embodiment, the main material has a maximum elongation in said transverse direction from equal to or less than 27% under a load of 10 N per cm width, in one embodiment equal to or less than 25% under a load of 10 N per cm width, in one embodiment equal to or less than 23% under a load of 10 N per cm width.

As indicated above, to facilitate comfort through e.g. lower supine (resting) pressures, main materials desirably have a difference quotient of tension in transverse direction from 15% elongation to 20% elongation that is shallower than the difference quotient of tension in transverse direction from 20% elongation to 25% elongation. In one embodiment, the difference quotient of tension in transverse direction from 15% elongation to 20% elongation is equal to or less than 70% of the difference quotient tension in transverse direction from 20% elongation to 25% elongation; in one embodiment equal to or less than 55% of the difference quotient tension in transverse direction from 20% elongation to 25% elongation, in one embodiment equal to or less than 45% of the difference quotient tension in transverse direction from 20% elongation to 25% elongation; in one embodiment equal to or less than 35% of the difference quotient tension in transverse direction from 20% elongation to 25% elongation.

In one embodiment, main materials have a differential quotient of tension in transverse direction from 25% elongation to 30% elongation is equal to or greater than 1.2 N per cm width per percent elongation, in one embodiment equal to or greater than 1.8 N per cm width per percent elongation, in one embodiment equal to or greater than 2.4 N per cm width per percent elongation, in one embodiment equal to or greater than 3.0 N per cm width per percent elongation. In one embodiment, main materials have a difference quotient of tension in transverse direction from 25% elongation to 30% elongation equal to or less than 24 N per cm width per percent elongation, in one embodiment equal to or less than 20 N per cm width per percent elongation, in one embodiment equal to or less than 16 N per cm width per percent elongation, in one embodiment equal to or less than 12 N per cm width per percent elongation.

Main materials in one embodiment show a tension in transverse direction at 30% elongation or at 30% elongation, after a one minute hold, equal to or greater than 10 N per cm width, in one embodiment equal to or greater than 15 N per cm width, in one embodiment equal to or greater than 20 N per cm width, in one embodiment equal to or greater than 25 N per cm width. In one embodiment, main materials show a tension in transverse direction at 30% elongation or at 30% elongation, after a one minute hold, equal to or less than 55 N per cm width, in one embodiment equal to or less than 50 N per cm width, in one embodiment equal to or less than 45 N per cm width, most particularly equal to or less than 40 N per cm width.

Desirably main material have a recovered elongation in transverse direction equal to or greater than 80%, in particular equal to or greater than 85%, more particularly equal to or greater than 90%, most particularly equal to or greater than 95%.

To facilitate the minimization and/or avoidance of compression device fatigue, main materials in one embodiment show an elongation rise in transverse direction equal to or less than 3.5%.

Desirably main materials are rather flexible to facilitate application as well as general fitting of the sleeve onto the relevant portion of the body part (e.g. limb, torso, neck, or head). In one embodiment, main materials show a bending length in the transverse and/or the longitudinal direction equal to or less than 20 cm, in particular equal to or less than 15 cm; in one embodiment equal to or less than 10 cm, in one embodiment equal to or less than 5.0 cm. Alternatively or in addition, in one embodiment main materials show a flexural rigidity in the transverse and/or the longitudinal direction equal to or less than 150 mN·cm, in one embodiment equal to or less than 125 mN·cm; in one embodiment equal to or less than 75 mN·cm, in one embodiment equal to or less than 35 mN·cm.

As indicated above, to facilitate desirable contour fitting of compression devices, in particular sleeves thereof, desirably main materials have elasticity in the longitudinal direction of the sleeve. In one embodiment, main materials show anisotropic elasticity characteristics where they are easier to stretch in the longitudinal direction. In one embodiment, main materials have a ratio of tension in transverse direction at 30% elongation (or at 30% elongation after a one minute hold) to tension in longitudinal direction at 30% elongation (or at 30% elongation after a one minute hold) which is greater than 1.8, in one embodiment equal to or greater than 2.0, in one embodiment equal to or greater than 2.2.

In one embodiment, main materials have a water vapor transmission rate equal to or greater than 2000 g/(m$^2$0.24 hours), in one embodiment equal to or greater than 2200 g/(m$^2$0.24 hours) from its inner to outer surface.

In one embodiment, main materials comprise a fibrous fabric, in particular a woven or knitted fabric, in one embodiment a knitted spacer fabric. Knitted spacer fabrics are three-dimensional knitted fabrics having two knitted substrates (e.g. a top layer and a bottom layer) which are joined together by spacer yarns (as an intermediate connecting layer). In one embodiment, such fabrics, in particular knitted spacer fabrics, have a basis weight equal to or greater than 100 g/m$^2$, in one embodiment equal to or greater than 150 g/m$^2$, in one embodiment equal to or greater than 200 g/m$^2$, in one embodiment equal to or greater than 250 g/m$^2$. In addition or alternatively thereto, such fabrics, in particular knitted spacer fabrics, have a thickness equal to or greater than 0.5 mm, in one embodiment equal to or greater than 1.0 mm, in one embodiment equal to or greater than 1.4 mm, and in one embodiment equal to or greater than 1.8 mm. In addition or alternatively thereto, such fabrics, in particular knitted spacer fabrics, may have a thickness equal to or less than 6.0 mm, in one embodiment equal to or less than 5.2 mm, in one embodiment equal to or less than 4.4 mm, and in one embodiment equal to or less than 3.6 mm. To minimize or avoid creation of impressions on the skin and/or a potential of skin irritation, in one embodiment fabrics, in particular knitted spacer fabrics, do not have large open patterns on the side of the fabric that will be facing the skin; in one embodiment at least in one direction (e.g. machine or cross direction) the breadth of opening(s) is equal to or less than 3 mm. In the other direction (e.g. cross or machine direction, respectively) the breadth may be equal to or less than 3 mm or alternatively greater than 3 mm. Warp knitted spacer fabrics have been found to be suitable. Warp-knitted spacer fabrics are typically knitted on a rib raschel machine having two needle bars. Examples of suitable warp-knitted spacer fabrics include the spacer fabric marketed by Gehring Textiles Inc., Garden City, N.Y. 11530, USA under the trade designation SHR 700/3 D3 D/0 7208810 and the spacer fabric marketed by Müller Textil, 51674 Wiehl, Germany under the trade designation 3 Mesh 5992.

Compression devices may be configured and arranged such that the area of the central region is at least 40% (in particular at least 45%, more particularly at least 50%) of the total area of the sleeve (when the device is not in use). In addition or alternatively thereto, compression devices may be configured and arranged such that at a height corresponding to two-thirds the height of sleeve from the lower edge to the upper edge, the central region of the sleeve extends 40% or more across the sleeve in its transverse direction (when the device is not in use).

In one embodiment, at least 85% (in particular at least 90%, more particularly at least 95%) of the total area of the central region of the sleeve is made of said main material (when the device is not use).

In the event the first and/or second lateral side regions include the same material as the central region, said material having the corresponding properties of a main material, due to the provision of the respective parts of the releasable closure system, attachment of an optional tongue and/or stiffeners generally the respective regions will not have the corresponding properties of a main material. As indicated above, typically the maximum elongation in the transverse direction under a load of 10 N per cm of the first and/or second lateral side regions of the sleeve will be lower (most often significantly lower approaching and possibly reaching 0% elongation) than the maximum elongation in the transverse direction under a load of 10 N per cm of the central region of the sleeve. In the event, the first and/or second lateral side regions do not comprise main material, but another material or materials, again relative to the device as a whole including the releasable closure system elements and/or other elements provided on the first and/or second lateral side regions, desirably the first and second lateral side regions are not more stretchable in the transverse direction than the central region. Moreover in one embodiment the first lateral side region and the second lateral side region show a maximum elongation in the transverse direction under a load of 10 N per cm that is equal to or less than the maximum elongation in the transverse direction under a load of 10 N per cm in the central region of the sleeve. It will be appreciated that first lateral side region and/or the second lateral side region may show a maximum elongation in the transverse direction under a load of 10 N per cm down to 0%. In addition or alternatively thereto, the first lateral side region and the second lateral side region may show a maximum elongation in the longitudinal direction under a load of 10 N per cm that is equal to or less than the maximum elongation in the longitudinal direction under a load of 10 N per cm in the central region of the sleeve. Similarly it will be appreciated that first lateral side region and/or the second lateral side region may show a maximum elongation in the longitudinal direction under a load of 10 N per cm down to 0%, FIG. 4 shows a top view of the exterior of another exemplary embodiment of a compression device (100) for use in applying compression to a body part, in particular a limb, of a user, while FIG. 5 shows a cross-sectional view of this exemplary embodiment. The device comprises a sleeve (1) for substantially covering a portion of the body part, in particular the limb, of a user, including an outer surface (3), an inner surface (4), an upper edge (7) and a lower edge (8) as well as two lateral side edges (9, 10) extending from its upper edge to its lower edge where in the transverse direction from the first lateral side edge (9) to the second lateral side edge (10) the sleeve comprises a first lateral side region (13), a central region (14) and a second lateral side region (15). The second lateral edge region of the sleeve is provided with a plurality of rings (16) in series between the upper and lower edges of the sleeve. Each ring is attached, in this particular exemplary embodiment fixedly attached, by a strap (17) that extends in substantially the transverse direction of the sleeve between the ring and the sleeve, in particular between the ring and the second lateral side region. Referring to the cross-sectional view in FIG. 4, it can be seen that the strap (17) is attached to the second lateral side region (15) of the sleeve (1), in particular onto the outer surface (3) of the sleeve at the second lateral side region. An elongate stiffener (32) that extends lengthwise between the upper and lower edges of the sleeve is provided at the proximal ends of the straps, i.e. in the second lateral side region (15) adjacent to the second lateral edge (10). The exemplary embodiment includes a tongue (5) attached at one of its lateral side edge to the inner surface (4) of the sleeve at the second lateral side region (15). Referring to FIG. 5, the tongue includes two elongate stiffeners (32) located between an inner foam layer (6) and outer fabric cover (26). The exemplary compression device further comprises a plurality of strip-shaped mechanical fastening tabs (2), one for each ring (16).

As indicated above, the exemplary embodiment in FIGS. 4 and 5 differs from the exemplary embodiment shown in FIGS. 1 to 3a in that the fastening tabs are releasably attached onto the outer surface at the first lateral side region (13) of the sleeve. Moreover, looking at the exemplary embodiment depicted in the FIGS. 4 and 5, it can be seen that the outer major surface (33) at the distal end portion (24) of each fastening tab (2) is provided with hook, stem and/or cup-shaped fasteners (25) and the outer major surface at the proximal end portion (22) as well as at the inner tab portion (23) of the fastening tabs has a structure or is provided with a structure (26) that is adapted to be engaged by said tab fasteners. In addition, the inner major surface (34) at the proximal end portion (22) of each fastening tab (2) is provided with hook, stem and/or cup-shaped fasteners (27) (these second tab fasteners may be identical or different to the first tab fasteners (25)) and the outer surface (3) at the first lateral side region (13) of the sleeve (1) has a structure or is provided with a structure (28) that is adapted to be engaged by the second tab fasteners (27). As can be appreciated from FIG. 4, typically the first lateral side region (13) is provided with the relevant engagement structure (28) by laminating an appropriate layer of material onto the relevant region of the sleeve. In addition, the first lateral side region (13) can be easily trimmed along its outer edge. In the event, it is needed or desired to reduce the width or circumference of the compression device, in particular the sleeve thereof, the fastening tabs can be detached, an appropriate amount of the first lateral side region can be trimmed off, so as to achieve the needed or desired width/circumference. Thereafter the fastening tabs can be re-attached to the remaining portion of the first lateral side region, and the device applied. Generally, the tabs are attached to the outer surface of the sleeve such that the tabs extend across the first lateral side edge, in particular so that their distal end portions are displaced from first lateral side edge.

From FIG. 5, it will be appreciated that like the exemplary embodiment depicted in FIGS. 1 and 2, the three regions (13, 14, and 15) of the sleeve comprise the same material (30), i.e. main material. Similar to the first exemplary embodiment, due to the attachment of a stiffener (32), the ring-straps (17) and tongue (5) to the sleeve at the second lateral side region (15) the properties of the underlying main material in this region will be normally affected (i.e. the maximum elongation in the transverse direction under a load of 10 N per cm of the sleeve in the second lateral side region will be lower (often significantly lower approaching 0%) than the maximum elongation in the transverse direction under a load of 10 N per cm of the sleeve in the central region). Due to lamination of the fastener-engagement material (28) onto the outer surface at the first lateral side region (13), the properties of the underlying main material in this region may be affected. Moreover the overall properties of the first lateral side region will accordingly depend on the properties of the fastener-engagement material and thus the properties of the resulting laminate including the fastener-engagement-material and main material. In one embodiment, the fastener-engagement material and lamination method is selected so that the properties of the main material dictate the overall properties of the first regional side region. Nonetheless a number of the fastener-engagement materials available on the market are inelastic or essentially inelastic. If the applied fastener-engagement material is inelastic or (if not inelastic per se) has a lower maximum elongation under a load of 10 N per cm than the main material, it will be appreciated that the maximum elongation in the transverse direction under a load of 10 N per cm of the sleeve in the first lateral side region will be either zero or (if not zero) lower than the maximum elongation in the transverse direction under a load of 10 N per cm of the sleeve in the central region.

The exemplary embodiment in FIGS. 4 and 5 also differs from the exemplary embodiment shown in FIGS. 1 to 3a in that the straps favorably comprise a loop-indicating configuration.

For embodiments including rings with straps, it is favorable that at least a portion of said strap is expandable in at least the transverse direction, said expandable portion comprising a material having elasticity in at least the transverse direction and being configured and arranged, such that when the expandable portion is in its non-expanded state there is exteriorly a loop of material rising outwardly and when, in use under the provision of tension in the transverse direction of the sleeve, the expandable portion expands in the transverse direction and the loop flattens. This expandable portion having in its non-expanded state a loop of material to the exterior and rising outwardly, which in use under the provision of tension in the transverse direction of the sleeve, expands in the transverse direction so that the loop flattens (eventually disappearing) is termed herein as a loop-indicating configuration. Such a loop-indicating configuration advantageously provides a visual indication towards the extent of extension, thus facilitating assessment of the extent of extension and the provision of a good anatomic fit. Moreover, when there is no extension or only partial extension of the expandable strap portion, the outwardly facing loop will be fully raised or only partly flatten, and thus visible as such, and when there is full extension of the expandable strap portion the outwardly facing loop will disappear (i.e. it will flatten to such an extent there is no longer a loop of material rising outwardly). Such a visual indication is advantageous during the application because once the loop fully flattens out (and thus disappears) there is full extension and thus an indication towards sufficient anatomical fit. Moreover, by providing such a loop-indicating configuration in the straps of the plurality of rings that are provided in series between the upper and lower edges of the sleeve or in the elongate, expandable gusset that extends substantially lengthwise between the upper and lower edges of the sleeve, it is possible to have a visual indication towards extent of extension and thus fit over respective height of the sleeve between its upper and lower edges, so that if desired and/or needed, the extent of tightening of an individual fastening tab threaded through its opposing ring or eyelet can adjusted facilitating the provision of a desirable anatomic fit over the portion of the body part (e.g. limb, torso, neck, head) of a user covered by the sleeve and thus in turn facilitating uniformity of compression. The loop-indicating configuration is also useful while the user is wearing the compression device. For example, if, as in fact is desired, the volume of the body part (e.g. limb, torso, neck or head) is reduced for example as a result of oedema reduction due to effective compression therapy, the extent of tension on the device and on the expandable strap-portion will be reduced and the previously flattened loop will then noticeably pucker outwardly forming a fully raised or somewhat flattened loop, depending on the extent of reduced tension and thus providing an indication that the device should be re-tightened or re-applied.

In one embodiment, the product of the modulus of elasticity of the loop material times the thickness of the loop material is at least 90% of the product of the modulus of elasticity of said main material times the thickness of the main material, in particular the product of the modulus of elasticity of the loop material times the thickness of the loop material is equal to or greater than the product of the modulus of elasticity of said main material times the thickness of the main material.

In FIGS. 4 and 5, it can be seen that each strap (17) include an expandable portion (21) that is configured with a loop (20) towards the exterior and rising outwardly. This is best seen in cross-sectional view shown in FIG. 5 which like FIG. 4 shows the exemplary compression not in use and thus shows the expandable strap portion in its non-expanded state. It can also be seen that the expandable portion of the strap favorably comprises two layers, an outer layer of material (18) and an inner layer of material (19) where both the inner-layer-material and outer-layer-material have elasticity in at least the transverse direction and wherein the inner layer of material is affixed to the outer layer of material, so as to provide a loop of outer-layer-material (i.e. loop (20)) above the inner layer. As result of this elasticity, the configuration of the attachment of the inner and outer-layer-materials to one another as well as the configuration of the attachment of the strap to the ring and onto the sleeve, the loop-containing portion (21) of the strap is expandable in at least the transverse direction. When the expandable portion of the strap is not expanded, i.e. in its non-expanded state, as shown in FIGS. 4 and 5, the loop (20) is visible as an elongate mound or hump. In use, when the device is applied onto the body part, in particular the limb, of a user, tension will be provided and accordingly the expandable portion (21) of the strap will expand in the transverse direction and the loop can and will flatten.

For those embodiments where the expandable portion of the strap includes two layers, favorably the product of the modulus of elasticity (in the transverse direction) of the inner-layer-material times the thickness of the inner-layer material is less than the product of the modulus of elasticity (in the transverse direction) of the outer-layer-material times the thickness of the outer-layer material. In one embodiment, the product of the modulus of elasticity of the inner-layer-material times the thickness of the inner-layer-material is at least a factor of two times, in one embodiment at least a factor of four times, lower the product of the modulus of elasticity of the outer-layer-material times the thickness of the outer-layer-material.

Generally, for compression devices including rings and straps having an expandable portion with a loop-indicating configuration as described above, desirably said expandable portion of the strap has in its non-expanded state a width relative to the transverse direction of the sleeve of at least 0.1 cm, in particular at least 0.5 cm. Desirably the expandable portion of the strap has in its non-expanded state a width relative to the transverse direction of the sleeve of at most 4 cm, more desirably at most 3 cm. In one embodiment, the expandable portion of the strap has in its expanded state at the point where the loop just fully flattens out a width relative to the transverse direction of the sleeve of at least 1 cm. In one embodiment, the expandable portion of the strap has in its expanded state at the point where the loop just fully flattens out a width relative to the transverse direction of the sleeve of at most 8 cm, more favorably at most 6 cm.

FIGS. 6 to 12 depict exemplary embodiments where the loop-indicating configuration is provided in an elongate, expandable gusset that extends substantially lengthwise between the upper and lower edges of the sleeve. Generally, for compression devices that include such a gusset, the gusset favorably extends a height corresponding to 70% up to 100% of the height of the sleeve from the upper to lower edge, more favorably the gusset extends from the upper to lower edges of the sleeve. Similar to the expandable portion of the strap described above, gussets comprise a material having elasticity in at least the transverse direction in the sleeve and are configured and arranged such that when the gusset is in its non-expanded state (e.g. when the compression device is not in use) there is to the exterior of the device a loop of material rising outwardly and when in use under the provision of tension in the transverse direction of the sleeve, the gusset expands in the transverse direction and the loop flattens (eventually disappearing).

FIG. 6 shows a top view of the exterior of an exemplary embodiment of a compression device (100) for use in applying compression to a body part, in particular a limb, of a user including instead of rings, eyelets, while FIG. 7 shows a cross-sectional view of this exemplary embodiment. The device comprises a sleeve (1) for substantially covering a portion of the body part, in particular the limb, of a user. The sleeve includes an outer surface (3), an inner surface (4), an upper edge (7), a lower edge (8) and two lateral side edges (9, 10). As in the other exemplary embodiments, in the transverse direction from the first lateral side edge (9) to the second lateral side edge (10) the sleeve comprises a first lateral side region (13), a central region (14) and a second lateral side region (15). The second lateral edge region of the sleeve is provided with either a plurality of eyelets (12; only one eyelet is labelled) in series between the upper and lower edges of the sleeve. As can be appreciated from the Figures, in particular FIG. 7, the second lateral edge region (15) also includes a stiffener (32) that is located between the eyelets (12) and the second lateral edge (10). The exemplary compression device further comprises a plurality of strip-shaped mechanical fastening tabs (2), one fastening tab for each eyelet. The fastening tabs (2) as well as the first lateral side portion (13) is favorably configured as described above in conjunction with the exemplary embodiment shown in FIGS. 4 and 5. The exemplary device also includes a tongue (5) desirably affixed to the inner surface (4) at the second lateral edge region (15) so that the tongue underlies eyelets and extends outwardly from the second lateral edge (10). The tongue is configured as described above in conjunction with the exemplary embodiment shown in FIGS. 4 and 5. The sleeve also includes an elongate, expandable gusset (11) extending substantially lengthwise between the upper and lower edges (7, 8) of the sleeve, in particular the gusset extends from the upper to the lower edges of the sleeve. The gusset is expandable in at least the transverse direction of the sleeve and includes a loop (20) of material to the exterior and rising outwardly, which can be better seen in cross-sectional view shown in FIG. 7. It can also be seen that the expandable gusset (11) comprises two layers, an outer layer of material (18) and an inner layer of material (19), each said material having elasticity in at least the transverse direction. As can be appreciated from FIG. 7, the outer layer of the gusset is integral with the adjacent-lying material of the sleeve which is the main material (30). The inner layer of the gusset being a separate strip of material affixed to the inner surface of the sleeve, so as to provide a loop of outer-layer-material (i.e. the loop (20) of the gusset) above the inner layer. The loop (20) is visible as an elongate mound or hump. In use, when the device (100) is applied onto the body part, in particular onto the limb, of a user, tension will be provided and accordingly the expandable gusset (11) will expand in the transverse direction and the loop can and will flatten.

Gussets may be at least in part integral with adjacent lying sleeve material or alternatively gussets may be provided as inset into the sleeve (the exemplary embodiment depicted in FIGS. 8 and 9 is an example of the latter). When gusset is at least in part integral with adjacent lying sleeve material favorably that adjacent lying sleeve material is the main material such that the material of loop is the main material. For such cases, it will be appreciated then the loop material will normally have the same modulus of elasticity and thickness as the main material. Otherwise, it may be favorable that the product of the modulus of elasticity of the loop material times the thickness of the loop material is at least 90% of the product of the modulus of elasticity of said main material times the thickness of the main material, in particular the product of the modulus of elasticity of the loop material times the thickness of the loop material is equal to or greater than the product of the modulus of elasticity of said main material times the thickness of the main material.

For those embodiments where the expandable gussets includes two layers (e.g. an outer layer of material and an inner layer of material, each said material having elasticity in at least the transverse direction, where the inner layer of material is affixed to the outer layer of material, so as to provide a loop of outer-layer-material above the inner layer when the gusset is in its non-expanded state, which, in use under the provision of tension and accordingly expansion of gusset in the transverse direction, can flatten), favorably the product of the modulus of elasticity of the inner-layer-material times the thickness of the inner-layer-material being less than the product of the modulus of elasticity of the outer-layer-material times the thickness of the outer-layer-material. In one embodiment, the product of the modulus of elasticity of the inner-layer-material times the thickness of the inner-layer-material is at least a factor of two times, in one embodiment at least a factor of four times, lower than the product of the modulus of elasticity of the outer-layer-material times the thickness of the outer-layer-material. The two-layer gusset may be provided as an inset into the sleeve or alternatively, the outer layer of the gusset is integral with the adjacent-lying material of the sleeve with the inner layer of the gusset being a separate strip of material affixed to the inner surface of the sleeve. For the latter types of embodiments, i.e outer-layer is integral with the adjacent-lying sleeve material, in one embodiment that the adjacent-lying sleeve material is the main material, and once again for such embodiment it will be appreciated that the modulus of elasticity and the of the loop material, i.e. the outer-layer-material in the two-layer expandable gusset, will be normally equal to the modulus of elasticity and thickness of the main material. Otherwise as already indicated above, in one embodiment the product of the modulus of elasticity of the material of the loop (e.g. the outer-layer-material in two-layer gusset embodiments) times the thickness of the loop material is favorably at least 90% of the product of the modulus of elasticity of the main material times the thickness of the main material, in particular the product of the modulus of elasticity of the material of the loop times the thickness of the loop material is equal to or greater than the product of the modulus of elasticity of said main material times the thickness of the main material.

Although not shown in an illustration, it will be recognized that when the exemplary compression device depicted in FIGS. 6 and 7 is put to use covering the body part, in particular the limb, of a user (e.g. the lower leg including the calf of a user), the fastening tabs (2) will be passed through the eyelets (12), turned back and fastened onto themselves. The first lateral edge (9) will be thus drawn towards eyelets (12) and accordingly towards the second lateral edge (10) of the sleeve (1). Favorably the two lateral edges of the sleeve will not overlap, but will define an opening behind which the tongue (5) will be centrally positioned. Moreover in applying the compression device depicted in FIGS. 6 and 7, the sleeve (1) is positioned about the body part, in particular the limb, of the user, each of fastening tabs (2) is threaded through its opposing eyelet (12), turned back on itself and pulled such the first lateral side edge (9) of the sleeve is drawn towards the eyelets (12) so that the sleeve is tightened about the body part, in particular the limb, of the user, wherein the tab is pulled until the loop of the expandable gusset fully flattens out. Once the loop disappears, the fastening tabs are fastened so that the sleeve (and correspondingly the compression device) is restrained about the body part, in particular the limb, of the user.

Gussets desirably have in their non-expanded state a width relative to the transverse direction of the sleeve of at least 0.1 cm, more desirably at least 0.5 cm. Gussets desirably have in their non-expanded state a width relative to the transverse direction of the sleeve of at most 4 cm, more desirably at most 3 cm. In one embodiment, gussets have in their expanded state at the point where the loop just fully flattens out a width relative to the transverse direction of the sleeve of at least 1 cm. In one embodiment, gussets have in their expanded state at the point where the loop just fully flattens out a width relative to the transverse direction of the sleeve is at most 8 cm, in particular at most 6 cm.

Gussets may be provided anywhere in the sleeve between the fastening tabs and eyelets (or rings, for those embodiments including rings instead of eyelets). For ease in viewing loop-indicating configuration of the gusset while the device is being applied, suitably gussets may be provided in the central portion of the sleeve or in the second lateral side portion, more suitably in the central portion of the sleeve near the eyelets (or rings, if applicable) or in the second lateral side portion near or adjacent to the eyelets (or rings, if applicable) towards the central portion.

Returning to the exemplary embodiment depicted in FIGS. 6 and 7, it can be seen that the gusset is in the central portion (14) of the sleeve with the gusset being positioned near the eyelets (12) and thus distant to the fastening tabs (2) attached to the first lateral edge region (13) of the sleeve. Although not shown in an illustration, it will be appreciated that when this exemplary compression device (100) is in use on the body part, in particular the limb, of the user, the sleeve (1) will be disposed about a central axis (A), said central axis lying in a plane (P), and the gusset will extend along a third axis (G), wherein relative to a projection of this third axis (G) onto said plane (P) containing the central axis (A), the third axis (G) will be in parallel or essentially parallel alignment with the central axis (A). In alternative embodiments, gussets can be configured and arranged such that the aforesaid third axis (G) is inclined forming an acute angle ($\beta$) up to 25° inclusive relative to the central axis.

The exemplary compression device shown in FIGS. 8 and 9 is an example of an embodiment where the expandable gusset (11) is arranged such that when the compression device (100) is in use on the body part, in particular the limb, of the user, the gusset extends along a third axis (G), wherein relative to a projection of the third axis (G) onto said plane (P) containing the central axis (A), the third axis (G) is inclined forming an acute angle ($\beta$) relative to the central axis (A). In particular, the exemplary compression device shown in FIGS. 8 and 9 includes a sleeve (1) having instead of eyelets, a plurality of rings (16) in series between the upper and lower edges (7, 8) of the sleeve. Each ring is favorably fixedly attached by a strap (17) extending between the sleeve (1) and the ring (16). The rings of this exemplary device are positioned along the second lateral edge (10) of the sleeve and spaced apart from said edge and away from the second lateral edge region (15), in particular the lateral edge (39) of each ring which is near the second lateral edge (10) of the sleeve is spaced apart from the second lateral edge of the sleeve. In one embodiment, the spacing corresponds to a distance of at most 4 cm, more favorably at most 3 cm. Alternatively, rings may be positioned adjacent to the second lateral edge (but still away from the second lateral edge region (15)), in particular, the lateral edge (39) of each ring which is near the second lateral edge (10) of the sleeve may be positioned adjacent to the second lateral edge of the sleeve. From FIG. 9, it can be seen in this exemplary embodiment that the ring-straps are attached to the second lateral edge region (15) of the sleeve and the region (15) of the sleeve is provided with a stiffener (32). The exemplary embodiment includes fastening tabs (2) and a tongue (5), both elements configured and arranged as previously described above. In regard to the expandable gusset (11), it can be recognized from FIG. 9 that in this exemplary embodiment the gusset is provided as an inset provided in the sleeve, in particular in the central region (14) thereof. Moreover referring to the illustration of FIG. 9, it can be seen that the sleeve is made of two individual parts (1a and 1b) and that the gusset (11) comprises an outer layer of material (18) and inner layer of material (19), wherein the inner layer of material is affixed to the inner surface of the outer layer of material and configured and arranged so as to provide a loop (20) of outer-layer-material above the inner layer, and wherein the gusset is then affixed to inner surface (4) of the each of two sleeve parts (1a, 1b), thus bridging the two sleeve-parts to provide a complete sleeve with the loop (20) facing outwardly. As can be appreciated from the FIG. 9, each of the two sleeve parts (1a, 1b) includes main material (30) so that the central portion of the sleeve comprises for the most part main material, i.e. the central portion of the sleeve with the exception of the inset-gusset is made of the main material.

Figure 10A:
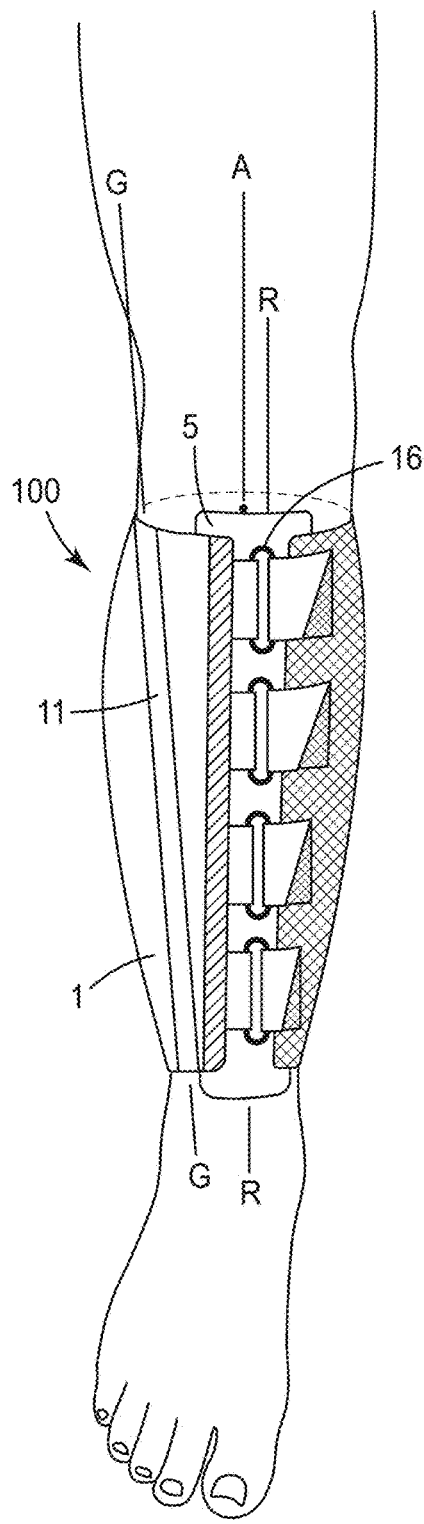
FIG. 10a shows a perspective, front view of the exemplary embodiment in depicted in FIGS. 8 and 9 in use on the lower leg of a user
Figure 10B:
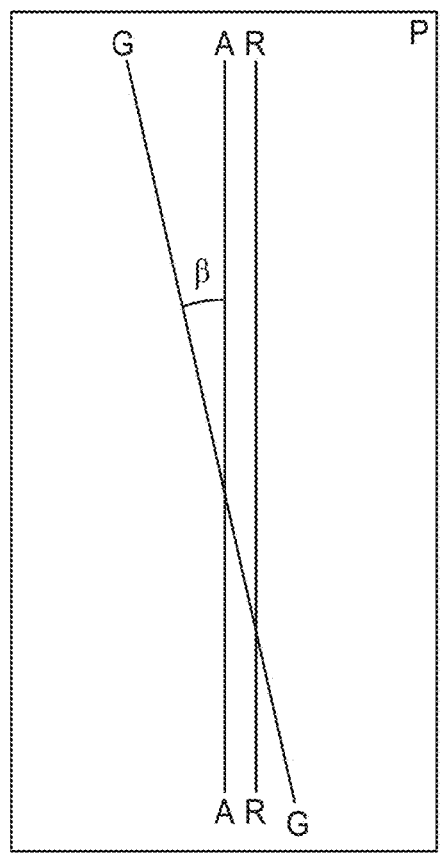
FIG. 10b shows a projection of the axes G and R (which are depicted in FIG. 10a) onto a plane P containing the central axis A (that is also depicted in FIG. 10a).

Referring to the illustration of FIG. 8, it can be seen that the gusset of this exemplary embodiment is inclined relative to e.g. the second lateral edge (10). Moreover, reference is made to FIG. 10a showing a perspective, front view of the exemplary compression device (100) depicted in FIGS. 8 and 9, in use on the lower leg of a user, it can be recognized that the sleeve (1) is disposed about a central axis (A) and the gusset (11) extends lengthwise along a third axis (G). Making reference to FIG. 10b showing a projection of this axis (G) on the plane (P) containing the central axis (A) it can be appreciated that relative to a projection of the third axis (G) onto said plane (P) containing the central axis (A), the third axis (G) is inclined forming an acute angle ($\beta$) of about 12° relative to the central axis. Returning to FIG. 10a, one can also see that when the compression device (100) is in use, the gusset (11) will expand in the transverse direction and the loop will flatten. As suggested in FIG. 10a, when the device is properly applied the gusset will be expanded such that the loop is fully flattened out, i.e. it disappears. It can also be appreciated from FIGS. 10a and 10b, that when the exemplary device is in use on the limb (e.g. the lower leg) of the user, the plurality of rings extends along a second axis (R), wherein relative to a projection of the second axis (R) onto said plane (P) containing the central axis (A), this second axis (R) is in parallel alignment or essentially parallel alignment relative to the central axis.

The exemplary compression device shown in FIGS. 11 and 12 is a variant of the exemplary embodiment shown in FIGS. 8 and 9 and differing in two aspects: The first being that the gusset (11) is not provided an inset, but rather the outer layer (18) of the gusset (11) is integral with the adjacent-lying material of the sleeve (1), in this particular embodiment with the main material of the sleeve, with the inner layer (19) of the gusset being a separate strip of material affixed to the inner surface (4) of the sleeve. Secondly the gusset (11) extends lengthwise such that when the compression device (100) is in use on the body part, in particular on the limb, of the user, the gusset extends along a third axis (G), wherein relative to a projection of the third axis (G) onto said plane (P) containing the central axis (A), the third axis (G) is parallel or essentially parallel to the central axis.

Although not specifically shown in the exemplary embodiments depicted herein, compression devices described herein may be configured to include other structural elements, for example a foot portion extending from the sleeve, in particular extending from an appropriate portion of the lower edge of the sleeve. Such a foot portion may be configured and arranged in the form of a stir-up or alternatively such as foot portion may be configured to provide a more extensive covering of the foot. Moreover the sleeve and such a foot portion may be configured and arranged so as to provide a boot-like compression device, either closed or opened toed and/or either closed or opened heeled. Such a foot part may be provided integrally with the sleeve or alternatively as a separate component that can be attached to the sleeve by an appropriate fastening means, such as buttons, mechanical fasteners and the like. Compression devices may also include bladders or gel inserts to facilitate modification of circumferential size. In this regard, sleeves, for example, could be provided with double walls or interior pockets for such inserts so that such insert(s) may be inserted and/or removed as needed or desired.

The following examples further illustrate the practice of the present invention. The examples are not intended to limit the invention, which is defined in the appended claims.

Test Methods

Test Methodology for Elongation and Recovered Elongation

Elongation and Recovered Elongation were determined through measurements based on BS EN 14704-1:2005 "Determination of the elasticity of fabrics, —Part 1: Strip tests": Method A, Knitted Fabrics (see inter alia sections 8.2.2 & 9.2.1) with the following variations and/or conditions to given method:

(i) strip test specimens were cut with their length parallel to direction to be measured, i.e. strips were cut so that the length of specimen is parallel either to the direction of the material that would be in the transverse/circumferential direction of the sleeve (for determinations in said transverse direction) or to the direction of the material that would be in the longitudinal direction of the sleeve (for determinations in said longitudinal direction)

(ii) specimen size was 250 mm in length and 5 cm wide (see 8.2.2.1.1);

(ii) gauge length was set at 70 mm (see 9.2.1.1);

(iii) extension rate was set at 500 mm/min (as given in section 9.2.1.2);

(iv) required cycling limits were set to said gauge length and a fixed load of 10 N per cm width (which corresponds to 50 N for given specimen width) (see subsection 9.2.1.3);

(vi) on the first cycle as well as on final (i.e. fifth) cycle, the testing machine was set to hold at 10 N per cm width for 1 minute (see NOTE 2 of 9.3);

(vii) the recovery period was 30 min (see NOTE 3 of 9.3);

(vii) test specimens were preconditioned for 24 hours at 50% RH and 20° C.; and (viii) the number of test specimens were three, where then the arithmetic mean is reported;

and with the following results: (a) percent elongation (S) is [(extension (mm) at maximum force on the final cycle—initial length)/initial length]×100; (b) percent recovered elongation (D) is (100—un-recovered elongation in percentage) and percent un-recovered elongation (C) is [(Q-P)/P]×100 where Q is the distance between applied reference marks (mm) after specified hold and recovery periods following the $5^{th}$ cycle and P is the initial distance between reference marks (mm); (c) percent elongation rise due to time is [(elongation on the final cycle, after specified holding period—elongation on the final cycle, prior specified holding period (i.e. S))/elongation on the final cycle, prior specified holding period]×100.

Test Methodology for Tension

Tension was determined through measurements based on BS EN 14704-1:2005 "Determination of the elasticity of fabrics, —Part 1: Strip tests": Method A, Knitted Fabrics (see inter alia sections 8.2.2 & 9.2.1) with the following variations and/or conditions to given method:

(i) strip test specimens were cut with their length parallel to direction to be measured, i.e. strips were cut so that the length of specimen is parallel either to the direction of the material that would be in the transverse/circumferential direction of the sleeve (for determinations in said transverse direction) or to the direction of the material that would be in the longitudinal direction of the sleeve (for determinations in said longitudinal direction)

(ii) specimen size was 100 mm in length and 2.5 cm wide (see 8.2.2.1.1);

(ii) gauge length was set at 70 mm (see 9.2.1.1);

(iii) extension rate was set at 500 mm/min (as given in section 9.2.1.2);

(iv) required cycling limits were set to said gauge length and a fixed elongation of 30% (see subsection 9.2.1.3);

(v) during cycling and elongation up to fixed elongation of 30%, the forces measured at 10%, 15%, 20% and 25% elongation were recorded in addition to force measured at 30% elongation;

(vi) on the final (i.e. fifth) cycle, the testing machine was held at the maximum elongation (i.e. 30% elongation) for 1 minute (see NOTE 2 of 9.3);

(vii) test specimens were preconditioned for 24 hours at 50% RH and 20° C.; and (viii) the number of test specimens were three, where then the arithmetic mean is reported; and with the following results: (a) tension at 30% elongation is the recorded maximum force at 30% elongation from the final cycle divided by the width size (i.e. 2.5 cm) of the specimen; (b) tensions at 10%, 15%, 20% and 25% elongation were the forces recorded at 10%, 15%, 20% and 25% elongation during the final cycle divided by the width size (i.e. 2.5 cm) of the specimen; and (c) difference quotient of tension from a first percent elongation to a second percent elongation is [(tension at the second percent elongation—tension at the first percent elongation)/(second elongation in percentage-first elongation in percentage)].

Test Methodology for Water Vapor Transmission Rate

The water vapor transmission rate of fabrics was determined according to test method DIN EN ISO 15106-part 1:2005 "Determination of Water Vapour Transmission Rate—Part 1 Humidity Detection Densor Method" with the following parameters, conditions and/or variations to given method:

(i) 38° C.; water vapor difference 90%; relative humidity upper chamber 10%, relative humidity lower chamber 100% (see Table 1; parameter set 2 in Section 8);

(ii) a reference specimen Core Tex, 5000 g/(m²·24 h), lot 071808; 16.11.2009;

(iii) circular diffusion area having a diameter of 10 mm;

(iv) number of test specimens were three (specimens were die-cut with a die having a cutting circle of 30 mm diameter, the aluminum barrier film was cut with a die having a cutting circle of 10 mm diameter; sample cards from MRS Seitter GmbH. Version: MRS 0225; lot no.: 100604 were used);

(v) test specimens were preconditioned for 24 hours at 50% RH and 23° C. prior to testing; and (vi) Easyperm WVPT 650M from Gintronic AG, Ruti, Switzerland, CH-8630 was used as measurement equipment; and with water vapor transmission rate reported in g/(m²·24h).

Test Methodology for Bending Length and Flexural Rigidity

The bending length and flexural rigidity of fabrics were determined according to test method ISO 9073-7 1$^{st}$ Edition 1995-12-15 "Textiles—Test methods for nonwovens Part 7: Determination of bending length" § Standard Test Method for Stiffness of Fabrics" with the following parameters and conditions:

(i) Specimen was 1 inch×8 inch (i.e. 25.4 mm×203.2 mm);

(ii) Specimens were pre-conditioned for 24 hours and tested at 21° C. and 65% RH;

(iii) Three specimens for each testing (machine and cross) direction was tested (MD corresponds to the longitudinal direction of the sleeve, while CD corresponds the transverse direction of the sleeve), where average value is reported;

(iv) Tests were performed using a M003B Shirley Stiffness Tester; and with bending length (C) in units of cm for each testing direction being equal to length of overhang divided by two and flexural rigidity (G), per unit width, in units of milliNewton centimeters being calculated using the equation $G=m\times C^3\times 10^{-3}$ where m is the mass of the test piece per unit area in g/m² and C is bending length in cm.

Materials:

M1: Warp knitted spacer marketed by Gehring Textiles Inc., Garden City, N.Y. 11530, USA under the trade designation SHR 700/3 D3 D/O 7208810, having the following characteristics:

100% polyester with a basis weight of 288 g/m² and a thickness of 2.3 mm;

outer layers made of multifilament yarns having a yarn diameter of approximately 200 μm and a single filament diameter of approximately 15 μm and a spacer layer made of monofilament yarn having a diameter of approximately 65 μm; and a knitted structure as shown in scanning electron and light microscopy images in FIG. 15 a to e.

In use, side 1 (i.e. that side shown in FIG. 15a) was used towards the interior of the device and side 2 (i.e. that side shown in FIG. 15b & c) was used towards the exterior of the device.

M2: Warp knitted spacer marketed by Müller Textil, 51674 Wiehl, Germany under the trade designation 3 Mesh 5992 having the following characteristics:

100% polyester with a basis weight of 380 g/m² and a thickness of approximately 2.6 mm;

outer layers made of multifilament yarns with a spacer layer made of a monofilament yarn of approximately 65 μm diameter;

the multifilament yarns of the first and second outer are different, for one side (side 1) the yarn diameter is approximately 400 μm with single filaments having diameters in the range of about 10 μm to about 22 μm, the majority in the range of about 16 μm to about 19 μm and for the other side (side 2) the yarn diameter is approximately 250 μm with single filaments of irregular shape having diameters in the range of about 10 μm to about 22 μm, the majority in the range of about 16 μm to about 19 μm; and a knitted structure as shown in scanning electron and light microscopy images in FIG. 16 a to d.

In use, side 1 (i.e. that side shown in FIG. 15a) was used towards the interior of the device and side 2 (i.e. that side shown in FIG. 16b) was used towards the exterior of the device.

CM1: Fabric of the compression product marketed by Circaid Medical Products, Inc. San Diego, Calif. 92123, USA under the trade designation JUXTACURES (product purchased in 2012);

CM2: Fabric of compression product marketed by FarrowMed, LLC, Texas 77803, USA under the trade designation FARROWWRAP Trim-to-Fit strong (product purchased in 2012):

CM3: Fabric used in the wrist-splint product marketed by 3M Futuro under the trade designation Reversible Splint Wrist ("Handgelenkschiene" product number 47855). Laminate of polyester knitted fabric/polyurethane foam/polyester knitted fabric from Rubberlite, Huntington W. Va. 25703, USA with a thickness of 3.1 mm and a weight of 600 g/m²: RP-M-767//0.075" Rubberlite S0702 Foam//RF-M-2877. The polyester fabrics RP-M-767 and RF-M-2877 are manufactured by Green Textiles, Spartanburg, S.C. 29301-4929, USA.

Material Properties Testing Results

TABLE 1

Determination of Elongation, Elongation Rise and Recovered Elongation in Transverse/Circumferential Direction

| Material | Elongation (%) at 10N per cm width At end of 5$^{th}$ cycle | Elongation (%) at 10N per cm width At end of 5$^{th}$ cycle & after 1 min hold | Elongation Rise (%) | Recovered Elongation (%) |
|---|---|---|---|---|
| M1- transverse | 18.3 | 18.9 | 3.3 | 95 |
| M2 - transverse | 21.4 | 21.8 | 1.9 | 99 |
| CM1 - transverse | 40.7 | 44.3 | 8.8 | 98 |
| CM2- transverse | 71.6 | 75.6 | 5.6 | 95 |
| CM3 - transverse | 32.7 | 34.0 | 4.0 | 98 |

TABLE 2

Determination of Elongation, Elongation Rise and Recovered Elongation in Longitudinal Direction

| Material | Elongation (%) at 10N per cm width At end of 5$^{th}$ cycle | Elongation (%) at 10N per cm width At end of 5$^{th}$ cycle & after 1 min hold | Elongation Rise (%) | Recovered Elongation (%) |
|---|---|---|---|---|
| M1- long | 29.4 | 30.3 | 3.1 | 94 |
| M2 - long | 34.4 | 34.8 | 1.2 | 98 |
| CM1 - long | 40.9 | 43.6 | 6.6 | 90 |
| CM2- long | 76.9 | 79.9 | 3.9 | 97 |
| CM3 - long | 60.1 | 63.4 | 5.5 | 93 |

TABLE 3

Determination of Tension in Transverse/Circumferential Direction

| Material | Tension (N per cm width) | | | | Tension after hold (N per cm width) |
|---|---|---|---|---|---|
| | 15% Elongation | 20% Elongation | 25% Elongation | 30% Elongation | 30% Elongation after 1 min hold |
| M1 - transverse | 0.3 | 2.8 | 11.9 | 31.2 | 24.3 |
| M2 - transverse | 0.7 | 3.3 | 11.4 | 34.1 | 26.1 |
| CM1 transverse | 2.7 | 4.3 | 6.3 | 9.1 | 6.9 |
| CM2 - transverse | 1.3 | 1.9 | 2.5 | 3.3 | 2.9 |
| CM3 - transverse | 1.6 | 2.8 | 4.6 | 7.5 | 6.1 |

Figure 17:
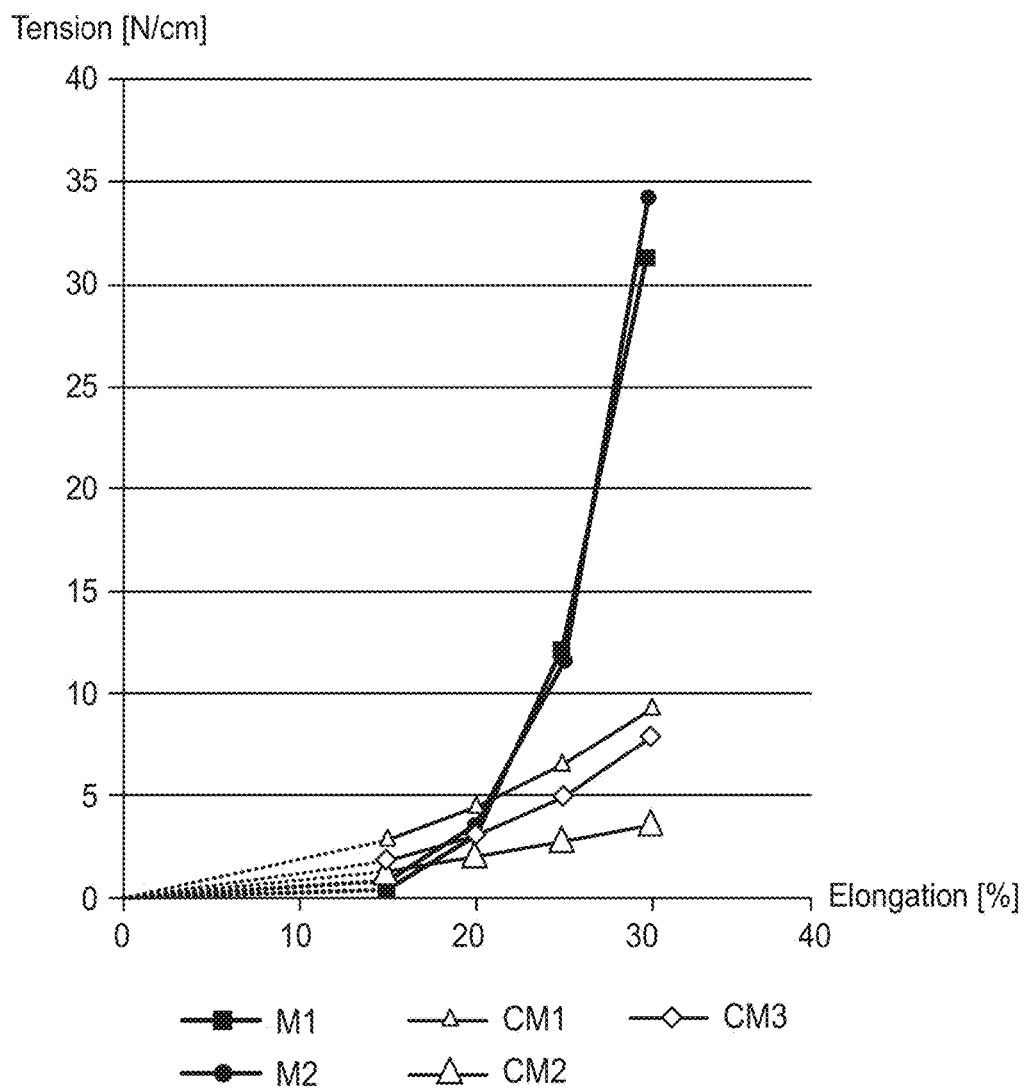
FIG. 17 represent a plot of tensions versus percent elongation for the five materials, M1, M2, CS1, CS2 and CS3, tested in the experimental section.

The results tension versus percent elongation determined in the final cycle are plotted in FIG. 17. The following table provides the difference quotients from a first elongation to a second elongation.

TABLE 4

Difference Quotients of Tension in Transverse/Circumferential Direction versus % Elongation

| Material | Difference Quotient (Δ N per cm width/Δ % elongation) | | |
|---|---|---|---|
| | 15%. to. 20% Elongation | 20%. to 25% Elongation | 25%. to 30% Elongation |
| M1 - transverse | 0.49 | 1.83 | 3.85 |
| M2 - transverse | 0.53 | 1.62 | 4.53 |
| CM1 transverse | 0.32 | 0.41 | 0.55 |
| CM2 - transverse | 0.12 | 0.13 | 0.15 |
| CM3 - transverse | 0.25 | 0.35 | 0.59 |

TABLE 5

Determination of Tension in Longitudinal Direction

| Material | Tension (N per cm width) | | | | Tension after hold (N per cm width) |
|---|---|---|---|---|---|
| | 15% Elongation | 20% Elongation | 25% Elongation | 30% Elongation | 30% Elongation after 1 min hold |
| M1 - long | 0.7 | 2.0 | 4.7 | 10.9 | 8.6 |
| M2 - long | 0.7 | 1.4 | 2.8 | 6.7 | 5.4 |
| CM1 long | 2.5 | 4.7 | 7.9 | 12.9 | 9.3 |
| CM2 - long | 1.4 | 2.4 | 3.9 | 6.0 | 4.7 |
| CM3 - long | 1.1 | 1.9 | 2.9 | 4.3 | 3.5 |

TABLE 6

Tension Ratio - Transverse/Circumferential versus Longitudinal Direction and vice versa

| Material | Tension Ratio Transverse/Longitudinal | | Tension Ratio Longitudinal/Transverse | |
|---|---|---|---|---|
| | 30% Elongation | 30% elongation after 1 min hold | 30% Elongation | 30% elongation after 1 min hold |
| M1 | 2.9 | 2.8 | 0.3 | 0.35 |
| M2 | 5.1 | 4.8 | 0.2 | 0.2 |
| CM1 | 0.7 | 0.7 | 1.4 | 1.3 |
| CM2 | 0.5 | 0.6 | 1.8 | 1.6 |
| CM3 | 1.8 | 1.8 | 0.6 | 0.6 |

TABLE 7

Determination of Water Vapor Transmission Rate -

| | WVTR (g/(m² · 24 h)) | |
|---|---|---|
| Material | from inside out[1] | from outside in[2] |
| M1 | 2571 | 2601 |
| M2 | 2498 | 2464 |
| CM1 | 1874 | 1569 |
| CM2 | 2187 | 2171 |
| CM3 | 1710 | 1850 |

[1]Here during WVTR-testing, the side of the material that would be on the interior of a compression device was placed towards the water vapor feed
[2]Here during WVTR-testing, the side of the material that would be on the exterior of a compression device was placed towards the water vapor feed

TABLE 8

Determination of Bending Length and Flexural rigidity

| Material | Bending Length (cm) | Flexural rigidity (mN · cm) |
|---|---|---|
| M1, (CD, transverse) | 3.5 | 12.3 |
| M1, (MD; longitudinal direction) | 4.4 | 24.5 |
| M2, (CD, transverse direction) | 3.9 | 22.5 |
| M2, (MD; longitudinal direction) | 3.5 | 16.3 |

Tests with Compression Devices
Test Methodology Using an Artificial Leg

A non-compressible artificial leg made out of plastic with a length of 35 cm between ankle (center) and lower end of the knee, a circumference of 24 cm just above the ankle and a circumference of 35.5 cm at the calf area (at the location of the measurements) was used to test compression devices. An inflatable air bladder placed between artificial leg and compression device was used to simulate leg volume expansion, for example the typical volume expansion when a person moves from a supine/rest position to a standing position. The artificial leg was first covered with a 35 cm long piece of white knitted polyester stockinet (3M Stockinet 7.6 cm×22.8 m (MS03; 70-2004-7301-8)) to facilitate uniform expansion and contraction of the bladder during expansion and evacuation. The bladder was fixed on the stockinet (see below) so that during test it was located between the stockinet and compression device. The circular pouch having a diameter of 110 mm that comes together with a sensor in a Kikuhime sub-bandage pressure equipment, received from TT MediTrade ApS, Søleddet 16, 4180 Sorø, Denmark was fitted to serve as the inflatable bladder. The bladder at its edge was fixed with two 4 cm long stripes of 3M Micropore tape on the stockinet on the front side (tibia) of the artificial leg and positioned so that it was centered where the circumference of the artificial leg is 355 mm. A Pico Press pressure sensor from MicroLab Elettronica, Italy, of approx. 50 mm diameter was fixed the same way on the stockinet at the calf region at the same leg height like the inflatable bladder. The tubes of sensor and bladder were led to the knee zone of the artificial leg and were secured with 3M Micropore tape, too. Via a valve the inflatable bladder was connected with bellows. The sensor was connected with a Pico Press pressure measurement unit from MicroLab Elettronica Sas, Roncaglia di Ponte San Nicolò (PD), Italy.

For the compression devices tested, two pen-marks were made on the outer surface on the device such that when the device is on the artificial leg the two marks are at the height corresponding to a circumferential line running through the centers of the bladder and sensor. For example in relation to a tested compression device having a design like that shown in FIG. 1, described in more detail below making reference to FIGS. 13 and 14, in this position the bladder is centered at a height in line with marks M' and M" and line $W_M$ in FIG. 13. The distance between the marks was at least 12 cm (in non-expanded state) and both marks were placed so that they were on the main compression material with only main compression material located there between. Moreover the marks were placed so that they were not on a closure system, a stiffener or any other subsidiary element to the main material.

All materials and equipment were exposed to ambient conditions (23° C.+−2° C.; 50%+−10% r.h.) within 24 hours prior to and during measurements.
Pressure at Supine/Rest Position The inflatable bladder was evacuated and empty, and the compression device to be tested was applied to the artificial leg and was then closed and tightened, such that a pressure of approximately 42 mmHg (+/−3 mmHg) was achieved (as measured with the Pico Press device).

The exact pressure was reported and designated as "pressure at rest". The artificial leg was positioned such that its own weight did not influence the pressure distribution at the locations of interest (i.e. for instance upright position and not laying).
Standing Pressure Thereafter the circumference around the compression device at the position where the sensor and the evacuated/empty bladder are attached was measured with a measuring tape. Then, the valve of the bladder was opened, the bladder was filled with air to such an extent that the circumference was increased by 1 cm (+−0.1 cm), and finally the valve of the bladder was closed. Again, the pressure was measured and recorded as the "standing pressure".
Stretched Reference Distance The shortest transverse/circumferential distance between the two marks on the outer surface of the tested compression device was measured with a measurement tape with an accuracy of +−1 mm and was designated as "stretched-reference-distance".

After this, the valve was opened and the bladder was evacuated. Then, the procedure was repeated within 10 minutes. The above mentioned values (pressure at rest, standing pressure and stretched-reference-distance) were measured again and were recorded. The reported values are an average of the two measurements.
Non-stretched Reference Distance Thereafter the compression device was taken off the artificial leg and after 30 minutes waiting time, the shortest transverse/circumferential distance between the marks was measured again and recorded as "non-stretched-reference-distance".

The "pressure difference" is the difference between "standing pressure" and "pressure at rest" and is a measure for the stretch resistance of the device. The percent "device-stretch" value is (stretched-reference-distance value minus the non-stretched-reference-distance) divided by non-stretched reference-distance times 100. (Note: the shortest distance between the marks M' and M" in the flat, laid opened device is a straight line. When the device is applied, the line (which could be marked on the device), along which the shortest distance between same marks is then measured, may not exactly congruent with the above mentioned straight line. While this could be considered as to cause a certain, but small amount of inaccuracy of the calculated percent device-stretch, this is negligible since all the tested devices were measured that same way.

Tested Compression Devices:

S1: Compression Device according to prototype design shown in FIGS. 13 and 14 and described below using material M1 as main material.

CS1: Compression product marketed by Circaid Medical Products, Inc. San Diego, Calif. 92123, USA under the trade designation JUXTACURES (product purchased in 2012);

The device was customized according to the manufacturer's instructions to fit the used artificial leg. Referring to Figure tin WO 2011/066237 the spine portion was attached to the body portion so that the spine curve was positioned such that its upper edge was located at a position of 36 cm and its lower edge at a position of 24 cm and excess material of the body portion was thereafter trimmed away.

CS2: Compression product marketed by FarrowMed, LLC, Texas 77803, USA under the trade designation FARROWWRAP Trim-to-Fit strong (medium size) (product purchased in 2012): Referring to US 2005/0209545, this product consisting of a series of overlapping straps (10 cm in height) fixed in their middle along a central band. When applied, the straps overlap with approx. 50% in longitudinal direction resulting in two layers of material at the overlapping portions of the straps. Additionally, due to overlapping and fixing of the straps around the circumference there is a further material overlap and accordingly in some portions have three and even four layers of overlap. For the testing described below, a four strap product was used, the straps having an overall length in the transverse direction of 46 cm, 45 cm, 41 cm and 32 cm, respectively (the shortest strap positioned near the ankle and the longest near the knee):

CS3: Reference compression device according to prototype design shown in FIGS. 13 and 14 and described below using material CM3 as main material.

Prototype Design for S1 and Reference CS3

Figure 13:
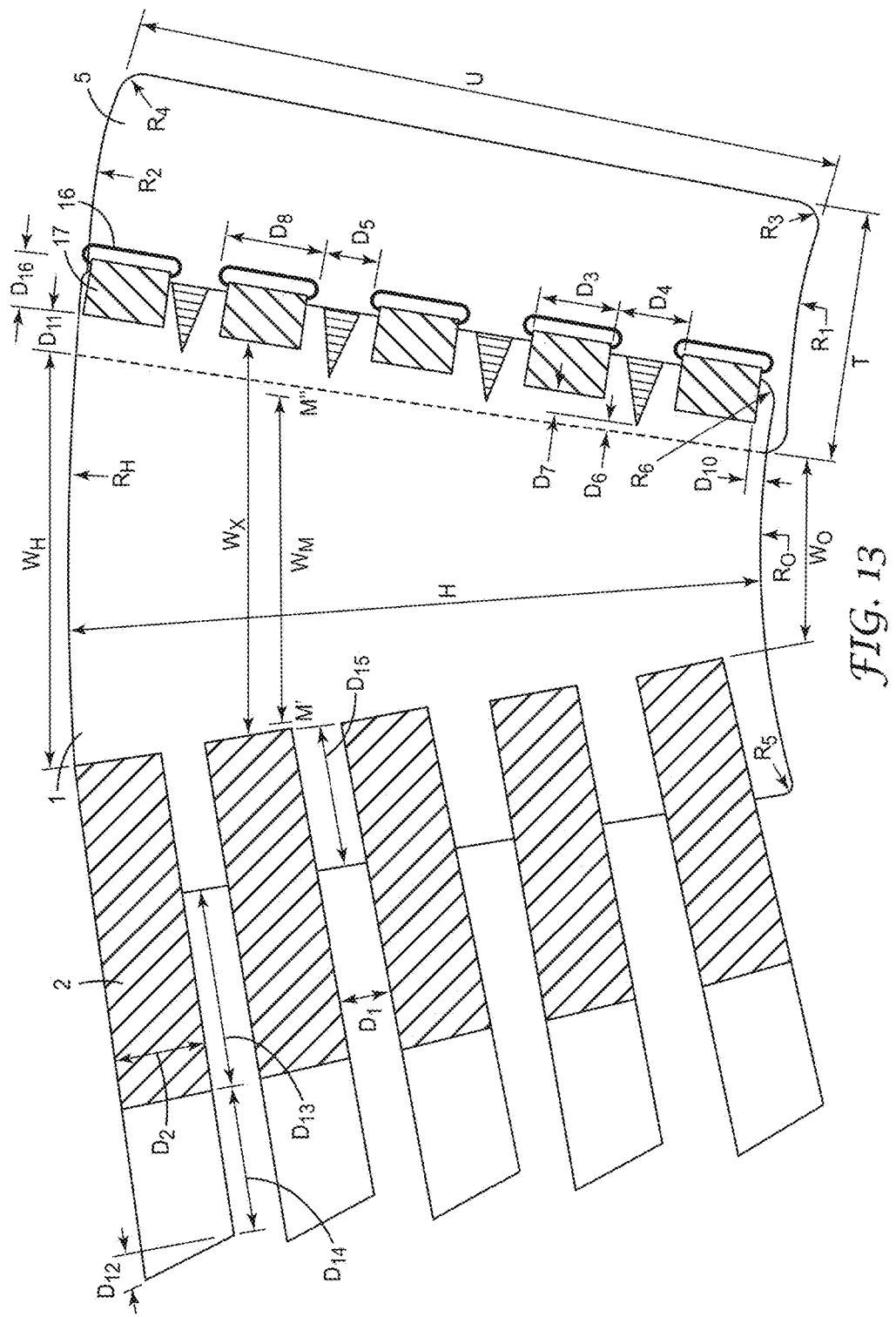
Figure 14:
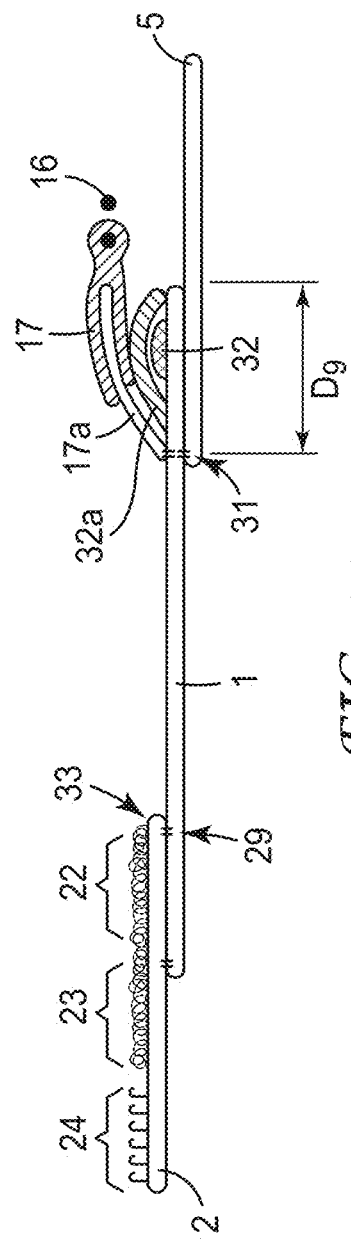
FIG. 14 shows a cross-sectional view of the prototype construction depicted in FIG. 13.
Figure 15A:
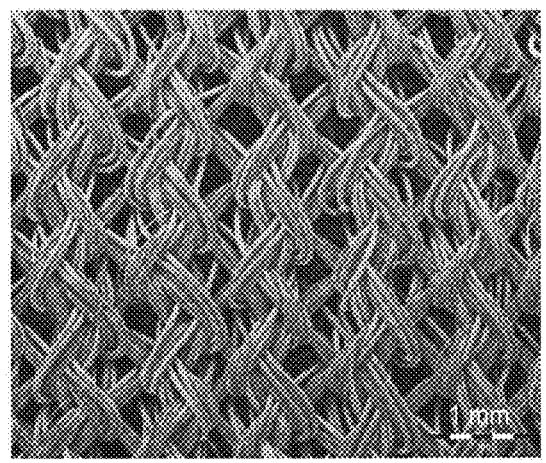
FIG. 15a shows the outer surface of one side (side 1)
Figure 15B:
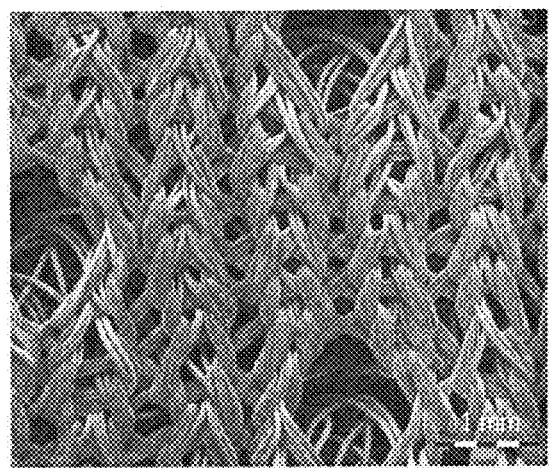
FIG. 15 a, b, d and e show SEM images and FIG. 15c a light microscopic image of the warp knitted spacer fabric marketed by Gehring Textiles Inc., Garden City, N.Y. 11530, USA under the trade designation SHR 700/3 D3 D/O 7208810 (M1), where
FIG. 15d shows a side view, machine direction
FIG. 15e shows a side view, cross direction.
Figure 15C:
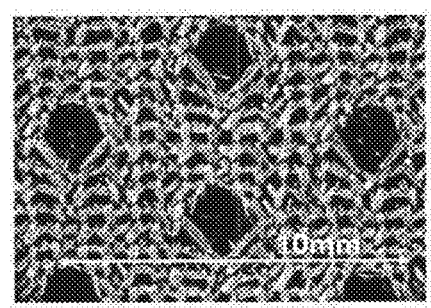
Figure 15D:
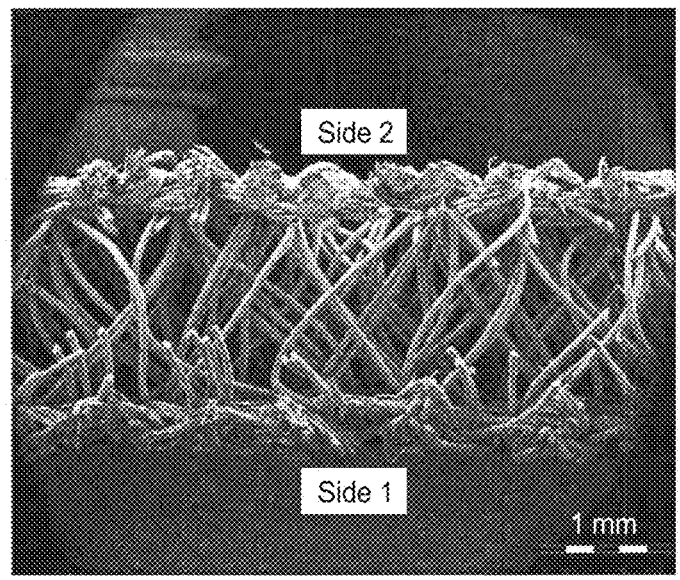
Figure 15E:
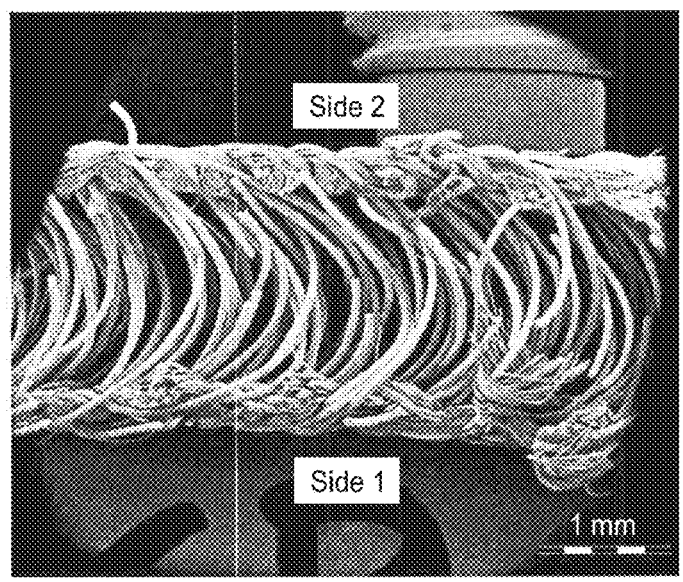
Figure 16A:
FIG. 16a shows the outer surface of one side (side 1)
Figure 16B:
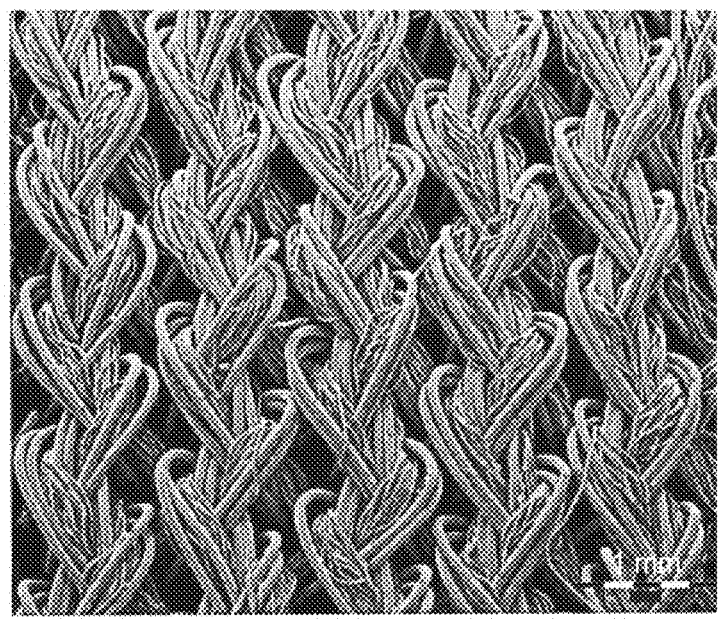
FIG. 16b shows the outer surface of the other side (side 2)
Figure 16C:
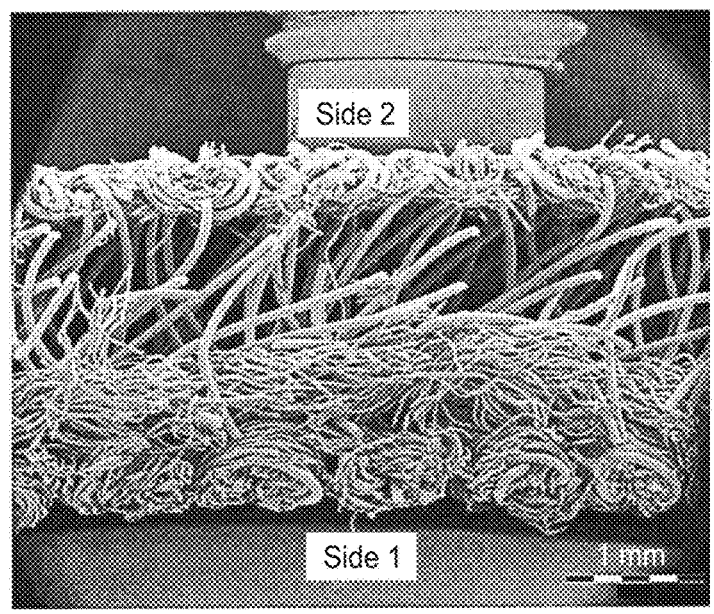
FIG. 16c shows a side view, machine direction
Figure 16D:
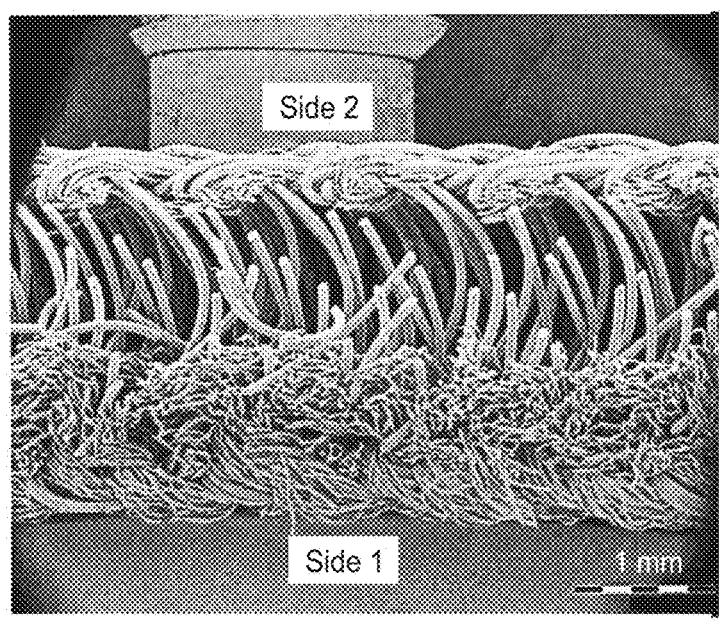
FIG. 16d shows a side view, cross direction.

S1 and CS3 were made according to the same design as shown in FIGS. 13 and 14, wherein the only difference was the main material of the two prototypes. In other words for S1 the main material was M1 and for CS3 the main material was CM3, while the closure system and all the other elements were the same. Referring to FIGS. 13 and 14, the following dimensions and materials were used:

| | | |
|---|---|---|
| $W_o$ = 70 mm | $R_2$ = 500 mm | $D_8$ = 57 mm |
| $W_H$ = 220 mm | $D_1$ = 22 mm | $D_9$ = 35 mm |
| $R_o$ = 150 mm | $D_2$ = 50 mm | $D_{10}$ = 17 mm |
| $R_H$ = 500 mm | $D_3$ = 50 mm | $D_{11}$ = $D_6$ + $D_7$ = 18 mm |
| H = 355 mm | $D_4$ = 22 mm | $D_{12}$ = 12 mm |
| $R_6 = R_5 = R_4 = R_3$ = 20 mm | $D_5$ = 15 mm | $D_{13}$ = 100 mm |
| U = 350 mm | $D_6$ = 8 mm | $D_{14}$ = 70 mm |
| $R_1$ = 150 mm | $D_7$ = 10 mm | $D_{15}$ = 90 mm |
| T = 140 mm | $D_{16}$ = 35 mm | |

Sleeve (1 in FIGS. 13 and 14) was made of material M1 or CM3, as described above.

Tongue (5 in FIGS. 13 and 14) was made from a foam-comprising laminate material obtained from Rubberlite, Huntington, W. Va. 25703, USA marketed under the trade designation VISCO TRI-VISCO (PU foam 3921130000) made of the following four layers (from the interior to the exterior): a) Black Polyester Jersey Fabric from Green Textile Association marketed under trade designation Style P-J-0035 401; b) polyurethane foam from Rubberlite marketed under the trade designation HYPUR-CEL T0812 (1.6 mm thick); c) polyurethane foam from Rubberlite marketed under the trade designation VISCO-CEL V0575 (2.4 mm thick); and d) Silver Polyester Jersey Fabric from Green Textile Association marketed under the trade designation SR-4816; said layers being laminated with a urethane curing hot-melt. The tongue was attached along one of its lateral edge to the inner surface of the sleeve at the second lateral side region by sewing.

Stiffener (32 in FIGS. 13 and 14) was a 1.6 mm thick thermoplastic duct material from 3M marketed under the trade designation SCOTCHCAST 72362; the material covering the stiffener (32a in FIGS. 13 and 14) is a suede-like, 100% cotton fabric.

Fastening strips (2 in FIGS. 13 and 14) were made by sewing an appropriate strip of a loop material from Velcro USA Incorporated marketed under the trade designation VELCRO Loop 1000 (22 and 23 in FIGS. 13 and 14) together with an appropriate strip a hook material from Velcro USA marketed under the trade designation VELCRO Hook 88 (24 in FIGS. 13 and 14). The fastening strips were attached onto the sleeve in the first lateral side region by sewing.

Oval rings (16 in FIGS. 13 and 14) were made of stainless steel; ring wire of 2.5 mm diameter, 6.9 mm inner width; 52 mm inner height, 3 mm inner radius of top and bottom, as illustrated in FIGS. 13 and 14 the rings were attached via straps (17 in FIGS. 13 and 14)) made of the aforesaid loop material by sewing onto an elongate strip (17a in FIGS. 13 and 14) of 100% polyester material, the elongate strip then attached by sewing onto the outer surface of the sleeve at the second lateral side region so the ring straps were located above and along the stiffener.

Yarn: 40-PermaCore, A&E: American & Efird LLC, Mt. Holly, N.C., USA for sewing the relevant components together.

When the devices S1 and CS3 were applied and closed but not yet tightened on the artificial leg, the width of the main material in circumference direction along the line marked $W_x$ in FIG. 13 was approximately 60% compared to the overall circumference of the device at the same height. As indicated above, when testing with the artificial leg, the sensor and bladder are positioned at the height corresponding to M', M" and $W_M$. It will be appreciated that the regions of the sleeve (i.e. the first and second lateral edge regions)

where the fastening strips, ring straps, stiffener and tongue were fixedly attached are non-stretchable or essentially non-stretchable. When the device was not in use, the central region of the sleeve, i.e. that region between the longitudinal, interior seams (29 in FIG. 14) connecting the fastening tabs to the sleeve and the seam (31 in FIG. 14) connecting the tongue and ring straps to the sleeve, had an area that was about 54% of the total area of the sleeve. The percent areas of the first and second lateral side regions were about 33% and 13%, respectively.

Results of Testing on Artificial Leg:

TABLE 9

Pressure measurements of tested devices

| Device | Pressure at rest[1] (mmHg) | Standing pressure[2] (mmHg) | Pressure difference (mmHg) |
|---|---|---|---|
| S1 | 43 | 75 | 32 |
| CS1 | 45 | 51 | 6 |
| CS2 | 34 | 48 | 4 |
| CS3 | 41 | 49 | 8 |

[1]inflatable bladder empty/evacuated
[2]inflatable bladder inflated so that the circumference is increased 1 cm

TABLE 10

Stretch and non-stretch measurements (between M' and M'') of tested devices

| Device | Non-stretched-reference-distance (cm) | Stretched reference-distance (cm) | Device-stretch (%) |
|---|---|---|---|
| S1 | 18.5 | 21.0 | 14 |
| CS1 | 23.0 | 26.0 | 13 |
| CS2 | 25.0 | 29.0 | 16 |
| CS3 | 16.5 | 20.8 | 26 |

Referring to the measured pressure, it can be seen that compression device S1 exhibits a significantly higher pressure difference than the other tested devices. In particular the pressure difference value for S1 is four times greater than that measured for the reference device CS3. Considering that S1 and CS3 differ only in the main material, i.e. M1 versus the reference material CM3, this demonstrates that the compression material M1 is particularly advantageous for use in compression therapy. Moreover, the results of the testing demonstrates that the use of such a main material having a low percent elongation at 10 N per cm width in conjunction with a high difference quotient of tension from 20% elongation to 25% elongation allows for advantageous stretch resistance and thus desirably high compression pressures for effective therapy.

A direct comparison between S1 to CS1 is somewhat complicated by the fact that the constructional designs of the compression devices are different. Moreover in CS1 at that height where the sensor and bladder were located, 14% of the circumference of the leg is covered with non-stretchable material, i.e. the non-stretchable closure system, while the remaining 86% is covered with the compression material of CS1, while the main compression material of S1 covers 60% at the same height (i.e. at the height corresponding to line $W_x$ in FIG. 13). So if CS1 had only covered 60% instead of 86% with the compression material of CS1 the pressure difference would be correspondingly roughly 1.5 times higher, i.e. around 9 mmHg. This value is significantly less than (about 3.5 times less) the pressure difference of S1.

Similarly a direct comparison between S1 to CS2 is somewhat complicated by the fact that the constructional designs of the compression devices are different, in particular the fact that at the height where the bladder and sensor were located, the straps of CS2 overlap providing at least two layers (again the ends of the straps form a three or four layer overlap). Moreover in CS2 at that height where the sensor and bladder were located, at least 2 layers of compression material of CS2 cover 86% of the circumference of the leg (i.e. the non-stretchable hook/loop closure system represents 14% of the circumference). If CS2 had covered in a single layer only 60% of the circumference of the leg, the pressure difference would be roughly the same or even slightly smaller, i.e. around 3 mmHg, i.e. 1.5 times higher due to circumferential difference but 2 times lower due to coverage by one layer instead of two layers.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A compression device for applying compression to a body part of a user comprising
a sleeve for substantially covering a portion of the body part of a user, wherein the sleeve has an outer surface, an inner surface, an upper edge, a lower edge and two lateral side edges, wherein in the transverse direction from the first lateral side edge to the second lateral side edge the sleeve comprises a first lateral side region, a central region and a second lateral side region, and wherein at least the central region of the sleeve comprises a main material having elasticity in at least the transverse direction of the sleeve, a maximum elongation in said transverse direction from 5% up to and including 30% under a load of 10 N per cm width, a difference quotient of tension in transverse direction from 20% elongation to 25% elongation equal to or greater than 0.6 N per cm width per percent elongation;
wherein the device further comprises a releasable closure system, said closure system being configured and arranged relative to the sleeve, such that, in use, upon closure of the closure system the sleeve is restrained and tightened about the body part of the user.

2. The compression device according to claim 1, wherein the closure system comprises a mechanical fastening closure system, and wherein the second lateral side region of the sleeve is provided with either a plurality of eyelets or a plurality of rings in series between the upper and lower edges of the sleeve, wherein the compression device further comprises a plurality of strip-shaped mechanical fastening tabs, wherein a single tab is provided for each eyelet or ring, as applicable, each tab comprising a proximal end portion and a distal end portion being connected by an inner tab portion, wherein said proximal end portion is releasably or fixedly attached to the first lateral side region of the sleeve such that the tab is located opposite to an eyelet or ring, as applicable, and extends in substantially the transverse direction of the sleeve with the distal end portion positioned away from the central portion of the sleeve, wherein each tab has a inner major surface located towards the outer surface of the sleeve and a outer major surface located away from the outer surface of the sleeve, wherein the outer major surface at the distal end portion of the tab comprises one part of a mechanical fastening system and said outer major surface at the proximal end portion of the tab comprise the complementary part of the mechanical fastening system; and wherein the tabs and eyelets or rings, as applicable, are configured and arranged such that, in use, the tabs are passed through the eyelets or rings, as applicable, then turned back on themselves such that the first lateral side edge of the sleeve is drawn towards the eyelets or rings, as applicable, and then fastened so that the sleeve is tightened and restrained about the body part of the user.

3. The compression device according to claim 2, wherein the sleeve is provided with a plurality of rings, and wherein each ring is releasably or fixedly attached by a strap extending between the sleeve and the ring in substantially the transverse direction of the sleeve, and wherein at least a portion of said strap is expandable in at least the transverse direction, said expandable portion comprising a material having elasticity in at least the transverse direction and being configured and arranged, such that when the expandable portion is in a non-expanded state there is exteriorly a loop of material rising outwardly and when, in use under the provision of tension in the transverse direction of the sleeve, the expandable portion expands in the transverse direction and the loop flattens.

4. The compression device according to claim 3, wherein the expandable portion of the strap comprises two layers, an outer layer of material and an inner layer of material, each said material having elasticity in at least the transverse direction, the product of the modulus of elasticity of the inner-layer-material times the thickness of the inner-layer-material being less than the product of the modulus of elasticity of the outer-layer-material times the thickness of the outer-layer-material, wherein outer-layer-material is said loop material and wherein the inner layer of material is affixed to the outer layer of material, so as to provide a loop of outer-layer-material above the inner layer when the expandable strap portion is in the non-expanded state, which, in use under the provision of tension and accordingly expansion of expandable portion of the strap in the transverse direction, can flatten.

5. The compression device according to claim 2, wherein the first lateral edge region of the sleeve is trimmable.

6. The compression device according to claim 1, wherein said main material has a difference quotient of tension in transverse direction from 15% elongation to 20% elongation that is equal to or less than 70% of the difference quotient tension in transverse direction from 20% elongation to 25% elongation; in particular equal to or less than 55% of the difference quotient tension in transverse direction from 20% elongation to 25% elongation, more particularly equal to or less than 45% of the difference quotient tension in transverse direction from 20% elongation to 25% elongation; most particularly equal to or less than 35% of the difference quotient tension in transverse direction from 20% elongation to 25% elongation.

7. The compression device according to claim 1, wherein said main material has a recovered elongation in transverse direction equal to or greater than 80%.

8. The compression device according to claim 1, wherein said main material has an elongation rise in transverse direction equal to or less than 3.5%.

9. The compression device according to claim 1, wherein said main material has at least one of
a tension in transverse direction at 30% elongation equal to or greater than 10 N per cm width, and
a tension in transverse direction at 30% elongation, after a one minute hold equal to or greater than 10 N per cm width.

10. The compression device according to claim 1, wherein said main material comprises a fibrous fabric.

11. The compression device according to claim 1, wherein the sleeve and closure system are configured and arranged such that in use, upon closure of the closure system, the two lateral edges of the sleeve are drawn towards one another, but do not overlap.

12. The compression device according to claim 1, wherein the closure system comprises a mechanical fastening closure system, and, wherein the first lateral side region and/or the second lateral side region are provided with a plurality of tabs, wherein each tab comprises a proximal end portion and a distal end portion, said proximal end portion being releasably or fixedly attached to the first lateral side region and/or second lateral side region of the sleeve, respectively, such that the tab extends across the first lateral side edge and/or the second lateral side edge, respectively, in substantially the transverse direction of the sleeve, with the distal end portion positioned away from the central portion of the sleeve, wherein each tab has a inner major surface, said inner major surface at the distal end portion of the tab comprises one part of a mechanical fastening system, and wherein at least the outer surface at the second lateral side region and/or the first lateral side region, respectively, opposite to each tab comprises the complementary part of the mechanical fastening system.

13. The compression device according to claim 1, wherein the sleeve includes an elongate, expandable gusset extending substantially lengthwise between the upper and lower edges of the sleeve, said gusset being expandable in at least the transverse direction of the sleeve, wherein said expandable gusset comprises a material having elasticity in at least the transverse direction and is configured and arranged, such that when the expandable gusset is in a non-expanded state there is exteriorly a loop of material rising outwardly, and when, in use under the provision of tension in the transverse direction of the sleeve, the expandable gusset expands in the transverse direction and the loop flattens.

* * * * *

UNITED STATES PATENT AND TRADEMARK OFFICE
CERTIFICATE OF CORRECTION

PATENT NO. : 10,058,457 B2
APPLICATION NO. : 14/780050
DATED : August 28, 2018
INVENTOR(S) : Schuren et al.

It is certified that error appears in the above-identified patent and that said Letters Patent is hereby corrected as shown below:

In the Specification

Column 4
Line 3-4, after "Tension"" insert -- . --.

Column 14
Line 6, delete "lymphodemia," and insert -- lymphedema, --, therefor.

Column 16
Line 35, delete "g/(m²0.24" and insert -- g/(m²•24 --, therefor.
Line 37, delete "g/(m²0.24" and insert -- g/(m²•24 --, therefor.

Column 17
Line 61, delete "0%," and insert -- 0%. --, therefor.

Column 27
Line 32, delete "Densor" and insert -- Sensor --, therefor.

Column 28
Line 22, delete "FIG." and insert -- FIGS. --, therefor.
Line 25, delete "FIG." and insert -- FIGS. --, therefor.
Line 45, delete "FIG." and insert -- FIGS. --, therefor.

Column 33
Line 32, delete "tin" and insert -- 1 in --, therefor.

Column 34
Line 17-30, delete "TRI-VISCO (PU foam 3921130000) made of the following four
layers (from the interior to the exterior): a) Black Polyester Jersey Fabric
from Green Textile Association marketed under trade designation Style P-J-0035

Signed and Sealed this
Eighteenth Day of December, 2018

Andrei Iancu
*Director of the United States Patent and Trademark Office*

CERTIFICATE OF CORRECTION (continued)
U.S. Pat. No. 10,058,457 B2

401; b) polyurethane foam from Rubberlite marketed under the trade designation HYPUR-CEL T0812 (1.6 mm thick); c) polyurethane foam from Rubberlite marketed under the trade designation VISCO-CEL V0575 (2.4 mm thick); and d) Silver Polyester Jersey Fabric from Green Textile Association marketed under the trade designation SR-4816; said layers being laminated with a urethane curing hot-melt. The tongue was attached along one of its lateral edge to the inner surface of the sleeve at the second lateral side region by sewing." and insert the same on Column 34, Line 16, as a continuation of the same paragraph. Line 49-55, delete "FIGS. 13 and 14 the rings were attached via straps (17 in FIGS. 13 and 14)) made of the aforesaid loop material by sewing onto an elongate strip (17a in FIGS. 13 and 14) of 100% polyester material, the elongate strip then attached by sewing onto the outer surface of the sleeve at the second lateral side region so the ring straps were located above and along the stiffener." and insert the same on Column 34, Line 48, as a continuation of the same paragraph.